(12) United States Patent
Yang et al.

(10) Patent No.: US 10,772,601 B2
(45) Date of Patent: Sep. 15, 2020

(54) ULTRASONIC IMAGING APPARATUS AND METHOD FOR CONTROLLING THE SAME

(71) Applicant: SAMSUNG MEDISON CO., LTD., Hongcheon-gun, Gangwon-do (KR)

(72) Inventors: Sun-Mo Yang, Seoul (KR); Sung-Jin Choi, Seoul (KR); Bong Koo Seo, Seoul (KR); Min Su Han, Seoul (KR)

(73) Assignee: SAMSUNG MEDISON CO., LTD., Hongcheon, Gangwon-Do (KR)

( * ) Notice: Subject to any disclaimer, the term of this patent is extended or adjusted under 35 U.S.C. 154(b) by 871 days.

(21) Appl. No.: 15/199,560

(22) Filed: Jun. 30, 2016

(65) Prior Publication Data

US 2017/0209118 A1    Jul. 27, 2017

(30) Foreign Application Priority Data

Jan. 21, 2016    (KR) .......................... 10-2016-0007646

(51) Int. Cl.
*A61B 8/08* (2006.01)
*A61B 8/00* (2006.01)
(Continued)

(52) U.S. Cl.
CPC ............ *A61B 8/4254* (2013.01); *A61B 5/055* (2013.01); *A61B 6/032* (2013.01); *A61B 6/037* (2013.01);
(Continued)

(58) Field of Classification Search
CPC ......... A61B 8/4254; A61B 5/055; A61B 8/08; A61B 8/54; A61B 6/032; A61B 8/461;
(Continued)

(56) References Cited

U.S. PATENT DOCUMENTS 5,828,770 A * 10/1998 Leis .................... G01S 5/163
                                                    382/103
9,459,087 B2 * 10/2016 Dunbar .................. G01B 7/003
(Continued)

FOREIGN PATENT DOCUMENTS

EP    1932477 A1    6/2008
JP    2003-190154 A    7/2003
WO    2013/001424 A2    1/2013

OTHER PUBLICATIONS

Extended European Search Report dated Jun. 16, 2017 issued in European Patent Application No. 16179098.5.
(Continued)

*Primary Examiner* — Joanne M Hoffman
(74) *Attorney, Agent, or Firm* — Morgan, Lewis & Bockius LLP

(57) ABSTRACT

An ultrasonic imaging apparatus and a method for controlling the same are disclosed, which relate to a technology for determining whether a position sensor mounted to an ultrasonic probe is separated from the ultrasonic probe. The ultrasonic imaging apparatus includes an ultrasonic probe, a plurality of position sensors mounted to the ultrasonic probe so as to acquire position information of the ultrasonic probe, and a control unit. The control unit determines whether at least one of a distance and a direction between the plurality of position sensors corresponds to at least one of a predetermined distance and a predetermined direction on the basis of coordinate information of the plural position sensors, and determines that at least one of the plural position sensors is separated from the ultrasonic probe when at least one of the distance and the direction does not correspond to at least one of the predetermined distance and the predetermined direction.

14 Claims, 17 Drawing Sheets

(a)

(b)

(51) Int. Cl.
*A61B 5/055* (2006.01)
*A61B 6/03* (2006.01)

(52) U.S. Cl.
CPC .............. *A61B 8/08* (2013.01); *A61B 8/4405* (2013.01); *A61B 8/4455* (2013.01); *A61B 8/461* (2013.01); *A61B 8/54* (2013.01); *A61B 8/4444* (2013.01); *A61B 8/58* (2013.01)

(58) Field of Classification Search
CPC ..... A61B 6/037; A61B 8/4405; A61B 8/4455; A61B 8/4444; A61B 8/58
See application file for complete search history.

(56) References Cited

U.S. PATENT DOCUMENTS

| | | | |
|---|---|---|---|
| 2006/0072124 A1* | 4/2006 | Smetak | A61B 5/06 356/614 |
| 2009/0266957 A1* | 10/2009 | Cermak | A61B 8/4245 248/225.11 |
| 2014/0024940 A1* | 1/2014 | Yoneyama | A61B 8/4254 600/443 |
| 2015/0112196 A1 | 4/2015 | Tanaka et al. | |
| 2015/0193962 A1 | 7/2015 | Ohuchi et al. | |
| 2016/0331351 A1* | 11/2016 | Guracar | A61B 8/463 |

OTHER PUBLICATIONS

European Communication dated Jun. 20, 2018 issued in European Patent Application No. 16179098.5.

\* cited by examiner (a)

(b)

(a)

(b)

(a) BEFORE SEPARATION (b) AFTER SEPARATION (a) BEFORE CORRECTION (b) AFTER CORRECTION

ULTRASONIC IMAGING APPARATUS AND METHOD FOR CONTROLLING THE SAME

CROSS-REFERENCE TO RELATED APPLICATION(S)

This application claims the benefit of Korean Patent Application No. 10-2016-0007646, filed on Jan. 21, 2016 in the Korean Intellectual Property Office, the disclosure of which is incorporated herein by reference.

BACKGROUND

1. Field

Embodiments of the present disclosure relate to an ultrasonic imaging apparatus and a method for controlling the same, and more particularly to a technology for determining whether a position sensor mounted to an ultrasonic probe is separated from the ultrasonic probe.

2. Description of the Related Art

An ultrasonic imaging apparatus applies an ultrasonic signal from the surface of an object (for example, a human body) to a target site of the inside of the body of the object, non-invasively acquires tomograms of soft tissues or images regarding blood flow using information of reflected ultrasonic signals (reflected ultrasonic echo signals), and is used for various medical purposes, for example, observation of the internal images of the target object, detection of foreign materials, etc.

The ultrasonic diagnostic apparatus has compact size and low price, displays a diagnostic image in real time, as compared to other image diagnostic apparatuses, for example, an X-ray diagnostic apparatus, an X-ray computed tomography (CT) scanner, a magnetic resonance imaging (MRI) apparatus, a nuclear medical diagnostic apparatus, etc. In addition, since the ultrasonic diagnostic apparatus does not cause radiation exposure, the ultrasonic diagnostic apparatus may be inherently safe. Accordingly, the ultrasonic diagnostic apparatus has been widely utilized in medical imaging fields as well as other imaging diagnosis devices.

The ultrasonic images obtained from the ultrasonic imaging apparatus may be matched with medical images obtained from other medical imaging apparatuses. Image registration (image matching) is a process for modifying different images and displaying the modified images on a single coordinate system. Image registration (image matching) may reconstruct two or more images into a single synthesized image. A user can recognize how to match different images with one another using image registration technology.

In order to compare images of a diseased part of the patient according to lapse of time or to compare images of a target object with images of normal tissues, image registration technology has been widely used in medical image diagnosis. In addition, in order to diagnose the presence or absence of a disease on the basis of images in which merits and demerits of different imaging modalities are reflected, image registration technology for representing several acquired images in the same space and comparing the acquired images with one another has been widely used.

In order to implement registration of such medical images, a position sensor for acquiring position information of an ultrasonic probe is used. In order to acquire correct position information for image registration, the position sensor must be correctly mounted to the ultrasonic probe, and must detect the position of the ultrasonic probe while simultaneously receiving less influence from the peripheral environment. Therefore, in recent times, many developers and companies are conducting intensive research into technology for determining whether the position sensor is not separated from the ultrasonic probe.

SUMMARY

Therefore, it is an aspect of the present disclosure to provide an ultrasonic imaging apparatus for calculating a distance between several position sensors mounted to an ultrasonic probe, comparing the calculated distance with a predetermined distance, and determining whether at least one position sensor is separated from the ultrasonic probe. It is another aspect of the present disclosure to provide an ultrasonic imaging apparatus for determining the presence or absence of an obstacle in a peripheral region of a position sensor on the basis of strength of signals received from several position sensors, and thus sensing the peripheral environment of an ultrasonic probe.

Additional aspects of the invention will be set forth in part in the description which follows and, in part, will be obvious from the description, or may be learned by practice of the invention.

In accordance with one aspect of the present disclosure, an ultrasonic imaging apparatus includes: an ultrasonic probe; a plurality of position sensors mounted to the ultrasonic probe so as to acquire position information of the ultrasonic probe; and a control unit configured to determine whether at least one of a distance and a direction between the plurality of position sensors corresponds to at least one of a predetermined distance and a predetermined direction on the basis of coordinate information of the plural position sensors, and to determine that at least one of the plural position sensors is separated from the ultrasonic probe when at least one of the distance and the direction does not correspond to at least one of the predetermined distance and the predetermined direction.

The plural position sensors may include a first position sensor and a second position sensor spaced apart from the first position sensor by a predetermined distance.

The ultrasonic imaging apparatus may further include: a reception unit configured to receive coordinate information of the plural position sensors on the basis of output signals of the plural position sensors.

The reception unit may receive an output signal of a field generator, and may receive coordinate information of the plural position sensors determined on the basis of the output signal of the field generator.

The reception unit may transmit the signal received from the field generator and at least one of the signals received from the plural position sensors to the control unit.

The reception unit may transmit coordinate information of the determined plural position sensors to the control unit.

The control unit may calculate not only a distance between a field generator and the first position sensor but also a distance between the field generator and the second position sensor on the basis of coordinate information of the first position sensor and coordinate information of the second position sensor.

The control unit may calculate a distance between the first position sensor and the second position sensor on the basis of coordinate information of the first position sensor and coordinate information of the second position sensor.

The control unit may compare the calculated distance between the first position sensor and the second position sensor with a predetermined distance.

If the calculated distance between the first position sensor and the second position sensor is shorter or longer than the predetermined distance according to the result of comparison, the control unit may determine that at least one of the first position sensor and the second position sensor is separated from the ultrasonic probe.

The control unit may determine whether the plural position sensors are separated from the ultrasonic probe by comparing strength of the signals received from the plural position sensors with predetermined signal strength.

The control unit may determine that the position sensor configured to output a signal having strength lower than the predetermined signal strength is separated from the ultrasonic probe.

The control unit may compare strength of the signals received from the plural position sensors with predetermined signal strength, and may determine that an obstacle is present in a peripheral region of any position sensor configured to output a signal having strength lower than the predetermined signal strength.

The ultrasonic imaging apparatus may further include: a display unit, if at least one of the plural position sensors is separated from the ultrasonic probe, configured to display separation or non-separation of the at least one position sensor.

The ultrasonic imaging apparatus may further include: a notification unit, if at least one of the plural position sensors is separated from the ultrasonic probe, configured to audibly indicate separation or non-separation of the at least one position sensor.

In accordance with another aspect of the present disclosure, a method for controlling an ultrasonic imaging apparatus includes: receiving coordinate information of a plurality of position sensors; determining whether at least one of a distance and a direction between the plurality of position sensors corresponds to at least one of a predetermined distance and a predetermined direction on the basis of coordinate information of the plural position sensors; and determining that at least one of the plural position sensors is separated from an ultrasonic probe when at least one of the distance and the direction does not correspond to at least one of the predetermined distance and the predetermined direction.

The receiving the coordinate information of the plurality of position sensors may include: receiving coordinate information of a first position sensor; and receiving coordinate information of a second position sensor spaced apart from the first position sensor by a predetermined distance.

The receiving the coordinate information of the plurality of position sensors may include: receiving an output signal of a field generator; and receiving coordinate information of the plural position sensors determined on the basis of the output signal of the field generator.

The method may further include: receiving an output signal of a field generator and at least one of output signals of the plural position sensors.

The method may further include: calculating not only a distance between a field generator and the first position sensor but also a distance between the field generator and the second position sensor on the basis of the coordinate information of the first position sensor and the coordinate information of the second position sensor, calculating a distance between the first position sensor and the second position sensor on the basis of coordinate information of the first position sensor and coordinate information of the second position sensor.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
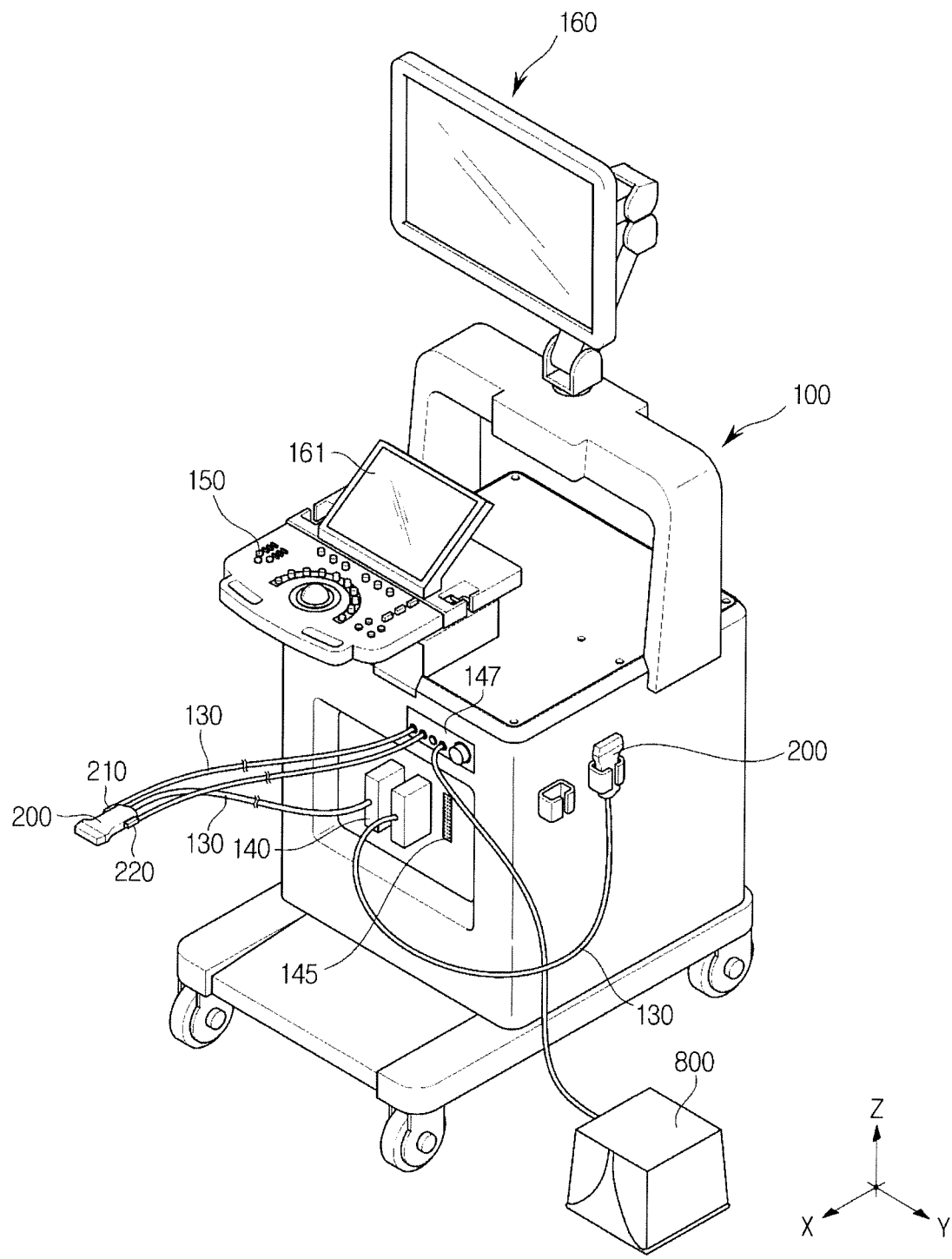
FIG. 1 is a view illustrating the appearance of an ultrasonic imaging apparatus according to an embodiment of the present disclosure.

Advantages and features of the present disclosure and a method of achieving the advantages and features of the present disclosure will be clearly understood from embodiments described hereinafter in conjunction with the accompanying drawings. Reference will now be made in detail to the embodiments of the present disclosure, examples of which are illustrated in the accompanying drawings, wherein like reference numerals refer to like elements throughout.

An ultrasonic imaging apparatus and a method for controlling the same according to embodiments of the present disclosure will hereinafter be described with reference to the attached drawings.

Throughout the specification of the present disclosure, if it is assumed that a certain part is connected (or coupled) to another part, the term "connection or coupling" means that the certain part is directly connected (or coupled) to another part and/or is electrically connected (or coupled) to another part through the medium of a third party. Throughout the specification of the present disclosure, if it is assumed that a certain part includes a certain component, the term 'comprising or including' means that a corresponding component may further include other components unless a specific meaning opposed to the corresponding component is written.

The target object may indicate organs of a human body, fetus, animals, metal, nonmetal, or some parts thereof. For example, the target object may include organs of the human body (e.g., a liver, a heart, a uterus, a brain, a breast, an abdomen) or blood vessels. The term "users" may indicate medical experts, for example, doctors, nurses, medical technologists, medical image specialists, ultrasonic inspectors, etc. In addition, the term "users" may also indicate technicians who repair medical devices. However, the scope or spirit of the present disclosure is not limited thereto.

The term "ultrasonic image" used in the entire specification of the present disclosure may denote images regarding the target object to be imaged using ultrasonic waves, and may also denote images regarding the target object using various diagnostic devices, for example, an X-ray diagnostic device, an X-ray CT scanner, an MRI (magnetic resonance imaging) device, and a nuclear medicine diagnostic device. In addition, the diagnostic devices to which the ultrasonic imaging apparatus and the method for controlling the same according to embodiments of the present disclosure can be applied may also be applied to an X-ray imaging device, an X-ray fluoroscopy device, a computed tomography (CT) scanner, a magnetic resonance imaging (MRI) device, a positron emission tomography (PET) device, and an ultrasonic imaging device. Although the embodiments will exemplarily disclose the ultrasonic imaging apparatus for convenience of description and better understanding of the present disclosure, it should be noted that the scope or spirit of the present disclosure is not limited thereto.

In addition, another term ' . . . part', ' . . . unit', 'module' or the like means a unit for processing at least one function or operation, and this unit may be implemented by hardware, software, or a combination thereof. As used in the specification and appended claims, the terms "a", "an", "one", "the" and other similar terms include both singular and plural forms, unless context clearly dictates otherwise.

Ultrasonic images acquired from the ultrasonic imaging apparatus may be image-matched with medical images obtained from other medical imaging apparatuses. Medical image matching (or medical imaging registration) may be achieved between heterogeneous images having different modalities. The user who views the ultrasonic images may have difficulty in definitely recognizing organs and lesions in real time, such that there is a need to perform matching (or registration) of heterogeneous images having different modalities.

In contrast, the MR or CT images cannot be acquired in real time during medical treatment whereas the user can clearly identify organs and lesions on the basis of the MR or CT images, such that breathing and movement of the patient are not reflected in the MR or CT images during medical treatment. The ultrasonic image has a higher recognition rate in soft tissues such as the liver or lungs as compared to hard tissues such as bones, and the CT image has a higher recognition rate in hard tissues as compared to soft tissues.

Therefore, there is a need to emphasize merits of respective images by matching images having different modalities. In order to perform image matching (or image registration) between heterogeneous medical images, the matching (or registration) position may be assigned to target medical images to be matched (or registered) using the ultrasonic probe, and the position assignment may be designated through the position sensor mounted to the ultrasonic probe.

In addition, the ultrasonic image is obtained through the ultrasonic probe. In this case, the position sensor mounted to the ultrasonic probe may be used to acquire and construct a three-dimensional (3D) ultrasonic image according to movement of the ultrasonic probe.

That is, the user may move the ultrasonic probe including the position sensor in various directions and angles, may perform ultrasonic diagnosis (based on freehand wobbling) of the target object on the basis of target object position information acquired by the position sensor, and may reconstruct the 3D ultrasonic image of the target object.

Further, the position sensor may be mounted not only to the ultrasonic probe, but also to other diagnostic devices or surgical operation devices. The position sensor may also obtain position information according to movement of the device not only in the ultrasonic image diagnosis but also in medical diagnosis and surgical operation of the target object.

If the user performs position setting for medical image matching using the ultrasonic probe, the position sensor may be separated from the ultrasonic probe. In this case, the separated position sensor may not establish the correct position for medical image matching. That is, if the position setting for medical image matching is achieved under the condition that the user does not recognize that the position sensor is separated from the ultrasonic probe, it is impossible to correctly perform the medical image matching due to incorrect position setting.

In addition, even when an object configured to affect a peripheral magnetic field of the ultrasonic probe is present or even when the environment affecting signals of the position sensor is constructed, the position sensor may not establish the correct position for medical image matching.

Accordingly, if the position sensor is separated from the ultrasonic probe or if an abnormal state occurs in the peripheral environment of the ultrasonic probe, the user must recognize the position sensor separation or the abnormal state occurrence and must interrupt the position setting procedure for medical image matching. However, the ultrasonic imaging apparatus according to the related art cannot determine whether the position sensor is separated from the ultrasonic probe such that the user who uses the conventional ultrasonic imaging apparatus cannot recognize separation or non-separation between the position sensor and the ultrasonic probe. In other words, whereas the conventional ultrasonic imaging apparatus can determine whether the position sensor normally operates by detecting only the change of signal strength of the position sensor, the conventional ultrasonic imaging apparatus cannot determine whether the position sensor is separated from the ultrasonic probe.

The ultrasonic imaging apparatus according to embodiments of the present disclosure can determine whether the position sensor is separated from the ultrasonic probe so as to inform the user of the determined result, and at the same time can determine signal strength of the position sensor and thus recognize the peripheral environment of the ultrasonic probe or the presence or absence of an obstacle in the peripheral region of the ultrasonic probe.

FIG. 1 is a view illustrating the appearance of an ultrasonic imaging apparatus according to an embodiment of the present disclosure.

Referring to FIG. 1, the ultrasonic imaging apparatus may include a main body 100, a reception unit 147 connected to the main body 100, an input unit 150, a display unit 160, a sub display panel 161, an ultrasonic probe 200, an ultrasonic probe 200, a first position sensor 210, and a second position sensor 220. The main body 100 of the ultrasonic imaging apparatus will hereinafter referred to as an ultrasonic imaging apparatus 100 for convenience of description and better understanding of the present disclosure.

Meanwhile, a plurality of casters (not shown) for movement of the ultrasonic imaging apparatus 100 may be mounted to a lower part of the ultrasonic imaging apparatus 100. The casters may fix the ultrasonic imaging apparatus to a specific position, or may move the ultrasonic imaging apparatus in a specific direction. The above-mentioned ultrasonic imaging apparatus is referred to as a cart-type ultrasonic imaging apparatus.

Alternatively, differently from FIG. 1, the ultrasonic imaging apparatus 100 may be a mobile (or portable) ultrasonic imaging apparatus that is capable of being carried by the user. In this case, the mobile ultrasonic imaging apparatus may not include casters therein. The mobile ultrasonic imaging apparatus may be implemented as any one of a picture archiving communication system (PACS) viewer, a smartphone, a laptop computer, a personal digital assistant (PDA), a tablet, etc., without being limited thereto.

The ultrasonic probe 200 configured to contact the skin of a target object may transmit and receive ultrasonic signals to or from the target object. In more detail, the ultrasonic probe 200 may generate ultrasonic signals according to input pulses, may transmit the generated ultrasonic signals to the inside of the target object, and may receive echo ultrasonic signals reflected from a specific part of the target object.

The ultrasonic imaging apparatus 100 may transmit ultrasonic signals to the ultrasonic probe 200, may receive echo ultrasonic signals from the ultrasonic probe 200, and may thus generate an ultrasonic image on the basis of the received resultant signals.

The ultrasonic image may be provided to a user through the display unit 160, and the user may visually recognize the received ultrasonic image of the interior part of the target object, such that the user can diagnose the target object (i.e., the patient).

The display unit 160 may also display various user interfaces (UIs) associated with control of the ultrasonic imaging apparatus 100. The user may confirm the UI received through the display unit 160, and may input either a control command for the ultrasonic imaging apparatus 100 or a control command for one constituent element of the ultrasonic imaging apparatus 100 through the input unit 150.

In addition, the display unit 160 may display ultrasonic images obtained from the ultrasonic diagnosis procedure. During the above-mentioned medical image matching, the display unit 160 may display the matched medical image thereon. The display unit 160 may be implemented as a Cathode Ray Tube (CRT), a Liquid Crystal Display (LCD), etc., or may also be implemented as any one of examples well known to those skilled in the art. The display unit 160 may also provide 2D images and 3D images as necessary.

The user may input a control command for the ultrasonic imaging apparatus by touching the display unit 160, and may also input a touch command for setting a user region of interest (to be observed or diagnosed by the user) in an ultrasonic image of the target object. The display unit 160 may include a touch panel to receive a user's touch input signal. The touch panel may be implemented as any one of a Liquid Crystal Display (LCD) panel, a Light Emitting Diode (LED) panel, an Organic Light Emitting Diode (OLED) panel, etc.

In addition, the display unit 160 may display specific information indicating whether at least one of the first position sensor 210 and the second position sensor 220 mounted to the ultrasonic probe 200 is separated from the ultrasonic probe 200, and may also display the change of signal strength of the first position sensor 210 and the second position sensor 220.

The sub display panel 161 may display various user interfaces (UIs) associated with control of the ultrasonic imaging apparatus in the same manner as in the display unit 160, and the user may confirm the UI received through the sub display panel 161, and may input either a control command of the ultrasonic imaging apparatus 100 or a control command of one constituent element of the ultrasonic imaging apparatus 100 through the input unit 150 or a touchscreen of the sub display panel 161.

In addition, the sub display panel 161 may display ultrasonic images obtained from the ultrasonic diagnosis procedure. The user touches the sub display panel 161, such that the user can input a control command of the ultrasonic imaging apparatus 100 or can input a command for setting a user interest region in an ultrasonic image. The sub display panel 161 may include a touch panel to receive a user's touch input command. The touch panel may be implemented as any one of a Liquid Crystal Display (LCD) panel, a Light Emitting Diode (LED) panel, an Organic Light Emitting Diode (OLED) panel, etc.

In the same manner as in the display unit 160, the sub display panel 161 may display specific information indicating whether at least one of the first position sensor 210 and the second position sensor 220 mounted to the ultrasonic probe 200 is separated from the ultrasonic probe 200, and may also display the change of signal strength of the first position sensor 210 and the second position sensor 220.

The input unit 150 may be configured to receive commands associated with the operation of the ultrasonic imaging apparatus 100. The user may input commands for performing various functions through the input unit 150. For example, the user may input commands for performing a diagnosis start function, a diagnosis part selection function, a diagnosis category selection function, a mode selection function of the final ultrasonic image, etc.

Through the input unit 150, the user may input a control command for medical image matching, and may also input a command for prestoring data regarding a reference distance to determine whether the first position sensor 210 and the second position sensor 220 are separated from the ultrasonic probe 200. Through the input unit 150, the user may input a command for prestoring data regarding reference strength of a specific signal that compares signals of the first position sensor 210 and the second position sensor 220 with a predetermined signal.

For example, as shown in FIG. 1, the input unit 150 may be located at the top of the main body 100. In this case, the input unit 150 may include at least one of a switch, a key, a wheel, a joystick, a track ball, and a knob.

The ultrasonic probe 200 may be connected to one end of the cable 130, and the other end of the cable 130 may be connected to a male connector 140. The male connector 140 connected to the other end of the cable 140 may be physically connected to a female connector 145 of the main body 100.

As described above, one ultrasonic probe 200 may be connected to one main body 100, and several ultrasonic probes 200 may also be connected to one main body 100 in a similar way to the above example. For this purpose, several female connectors may be mounted to the main body 100. As can be seen from FIG. 1, two ultrasonic probes 200 are connected to one main body 100.

Alternatively, differently from FIG. 1, the ultrasonic probe 200 may be wirelessly connected to the main body 100. In this case, the ultrasonic probe 200 may wirelessly transmit an echo ultrasonic signal corresponding to echo ultrasonic waves received from the target object to the main body 100.

The ultrasonic probe 200 may contact the skin of the target object, and thus transmit and receive ultrasonic signals to and from the target object. In more detail, the ultrasonic probe 200 may emit ultrasonic waves to the target object according to ultrasonic signals corresponding to electric signals received from the main body 100, may collect echo ultrasonic waves reflected from a specific part contained in the target object, and may transmit echo ultrasonic signals corresponding to the collected echo ultrasonic waves to the main body 100.

For this purpose, the ultrasonic probe 200 may include a transducer and a multiplexer (MUX) circuit. The transducer may include several elements which vibrate to convert an electric signal into an ultrasonic signal and vice versa. The elements may be arranged over one surface of the housing of the ultrasonic probe. In more detail, several transducers may be arranged in parallel to one or more apertures in a manner that ultrasonic signals can be transmitted and received through the apertures mounted to one surface of the housing.

The ultrasonic probe 200 may include a plurality of position sensors. The first position sensor 210 and the second position sensor 220 from among several position sensors may be mounted to the ultrasonic probe 200 so as to obtain position information of the ultrasonic probe 200. If necessary, one or more first position sensors 210 and one or more second position sensors 220 may be used, and the first position sensor 210 and the second position sensor 220 mounted to the ultrasonic probe 200 may be spaced apart from each other by a predetermined distance. In addition, the installation positions of the first and second position sensors (210, 220) are not limited thereto, the first and second position sensors (210, 220) may be implemented in various shapes, for example, the first and second position sensors (210, 220) may be contained in the ultrasonic probe 200 or mounted to the outside of the ultrasonic probe 200.

Each of the first position sensor 210 and the second position sensor 220 may include a slope sensor or the like, and may obtain position information of the ultrasonic probe 200. Position information of the ultrasonic probe 200 may include not only the spatial position of the ultrasonic probe 200 but also coordinate information of the ultrasonic probe 200. A method for obtaining position information of the ultrasonic probe 200 using the position sensor mounted to the ultrasonic probe 200 is well known to those skilled in the art, and as such a detailed description thereof will herein be omitted for convenience of description.

Each of the first position sensor 210 and the second position sensor 220 may be connected to one end of the cable 130, and the other end of the cable 130 may be connected to a coupling unit (not shown). The coupling unit (not shown) connected to the other end of the cable 130 may be physically coupled to the reception unit 147 contained in the ultrasonic imaging apparatus 100.

The reception unit 147 may be physically coupled to the first position sensor 210, the second position sensor 220, and the field generator 800. The reception unit 147 may receive signals from the first position sensor 210, the second position sensor 220, and the field generator 800, and may transmit the received signals to the control unit 400. In addition, the reception unit 147 may receive coordinate information from the first position sensor 210 and the second position sensor 220, and may transmit the received coordinate information to the control unit 400.

The reception unit 147 may be configured independently of the ultrasonic imaging apparatus 100, may be located outside the ultrasonic imaging apparatus 100, and may be implemented in a disc drive shape and then contained in the ultrasonic imaging apparatus 100. The number of cables 130 capable of being connected to the reception unit 147 is not limited thereto, and the reception unit 147 may be installed anywhere in the ultrasonic imaging apparatus 100 without departing from the scope or spirit of the present disclosure.

The field generator 800 may be located outside the ultrasonic imaging apparatus 100, and may be connected to the cable 130 and then physically connected to the reception unit 147. The field generator 800 may serve as a reference point for determining coordinate information of the first position sensor 210 and the second position sensor 220. The spatial coordinates of the first position sensor 210 and the second position sensor 220 may be determined on the basis of the position of the field generator 800.

The field generator 800 may transmit signals to the reception unit 147, and the reception unit 147 may receive coordinates of the first position sensor 210 and the second position sensor 220 on the basis of output signals of the field generator 800.

Figure 2:
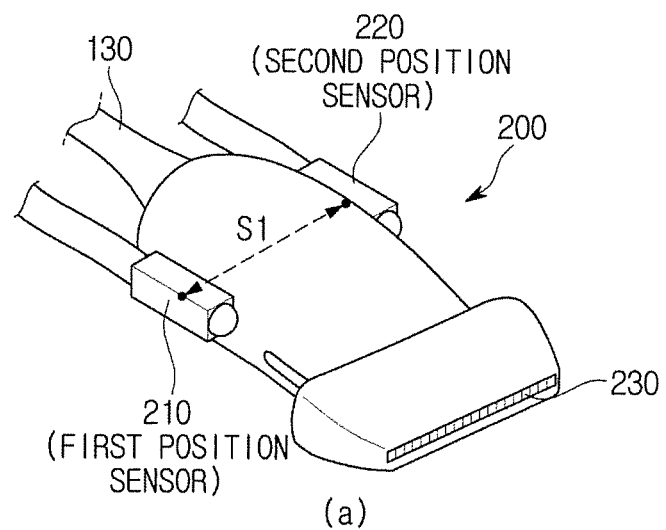
FIG. 2 is a view illustrating position sensors mounted to an ultrasonic probe according to an embodiment of the present disclosure.
Figure 2:
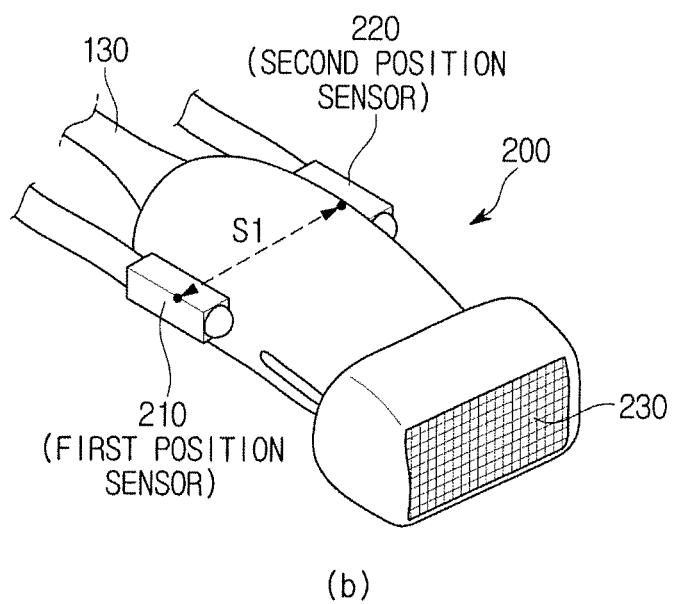
Figure 3:
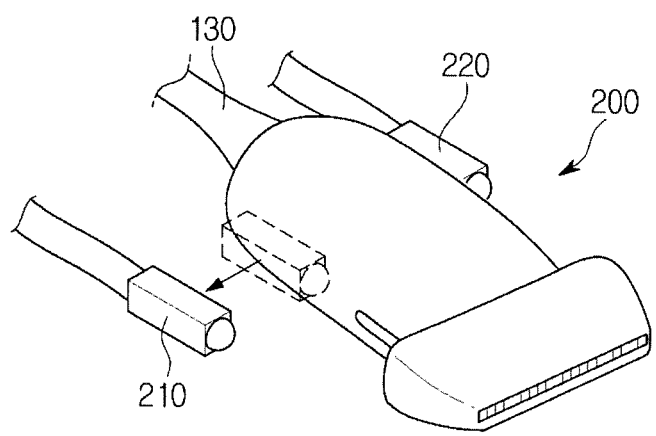
FIG. 3 is a view illustrating the position sensors separated from the ultrasonic probe according to an embodiment of the present disclosure.
Figure 3:
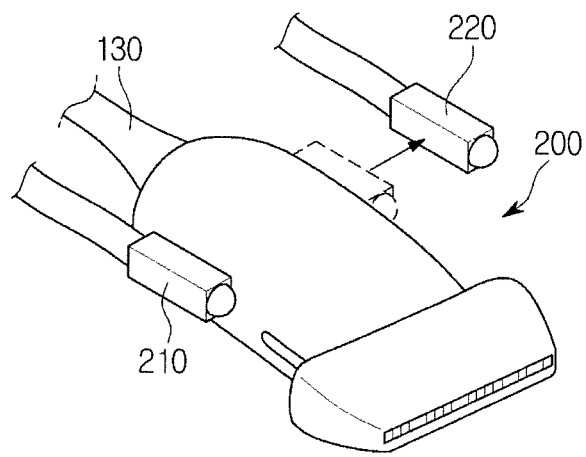

FIG. 2 is a view illustrating position sensors mounted to an ultrasonic probe according to an embodiment of the present disclosure. FIG. 3 is a view illustrating the position sensors separated from the ultrasonic probe according to an embodiment of the present disclosure.

Referring to FIG. 2, the ultrasonic probe 200 may be formed in various shapes according to various embodiments. A transducer array 230 contained in the ultrasonic probe 200 may include an one-dimensional (1D) transducer array as shown in FIG. 2(a), and may include a 2D transducer array as shown in FIG. 2(b).

Although the first position sensor 210 and the second position sensor 220 may be arranged at the side surfaces of the ultrasonic probe 200, the installation positions of the first position sensor 210 and the second position sensor 220 are not limited thereto, and the first position sensor 210 and the second position sensor 220 may be located anywhere in the ultrasonic probe 200 so as to acquire position information of the ultrasonic probe 200.

In addition, one or more first position sensors 210 and one or more second position sensors 220 may be used as necessary. The first position sensor 210 and the second position sensor 220 may be spaced apart from each other by a predetermined distance S1 or S2. In this case, the separation distance S1 or S2 between the first position sensor 210 and the second position sensor 220 may be stored in the storage unit 600 of the ultrasonic imaging apparatus 100. As described above, the control unit 400 may determine whether at least one of the first position sensor 210 and the second position sensor 220 is separated from the ultrasonic probe 200 on the basis of the distance (S1, S2) information stored in the storage unit 600.

In addition, the storage unit 600 may store mutual direction information between the first position sensor 210 and the second position sensor 220. The control unit 400 may determine mutual direction information between the position sensors when determining whether at least one of the first position sensor 210 and the second position sensor 220 is separated from the ultrasonic probe 200.

The first position sensor 210 and the second position sensor 220 are mounted to the ultrasonic probe 200, such that the user can acquire not only the spatial position of the ultrasonic probe 200 but also coordinate information of the ultrasonic probe 200 according to movement of the ultrasonic probe 200. In addition, each of the first position sensor 210 and the second position sensor 220 may be connected to one end of the cable 130.

Referring to FIG. 3, at least one of the first position sensor 210 and the second position sensor 220 may be separated from the ultrasonic probe 200. FIG. 3(a) exemplarily illustrates that the first position sensor 210 is separated from the ultrasonic probe 200, and FIG. 3(b) exemplarily illustrates that the second position sensor 220 is separated from the ultrasonic probe 200.

If the user establishes the position for medical image matching using the ultrasonic probe 200, at least one of the first position sensor 210 and the second position sensor 220 may be separated from the ultrasonic probe 200. In this case, correct coordinate information of at least one of the first position sensor 210 and the second position sensor 220 cannot be applied to the control unit 400, such that the user must recognize the separated one of the first and second position sensors (210, 220).

Figure 4:
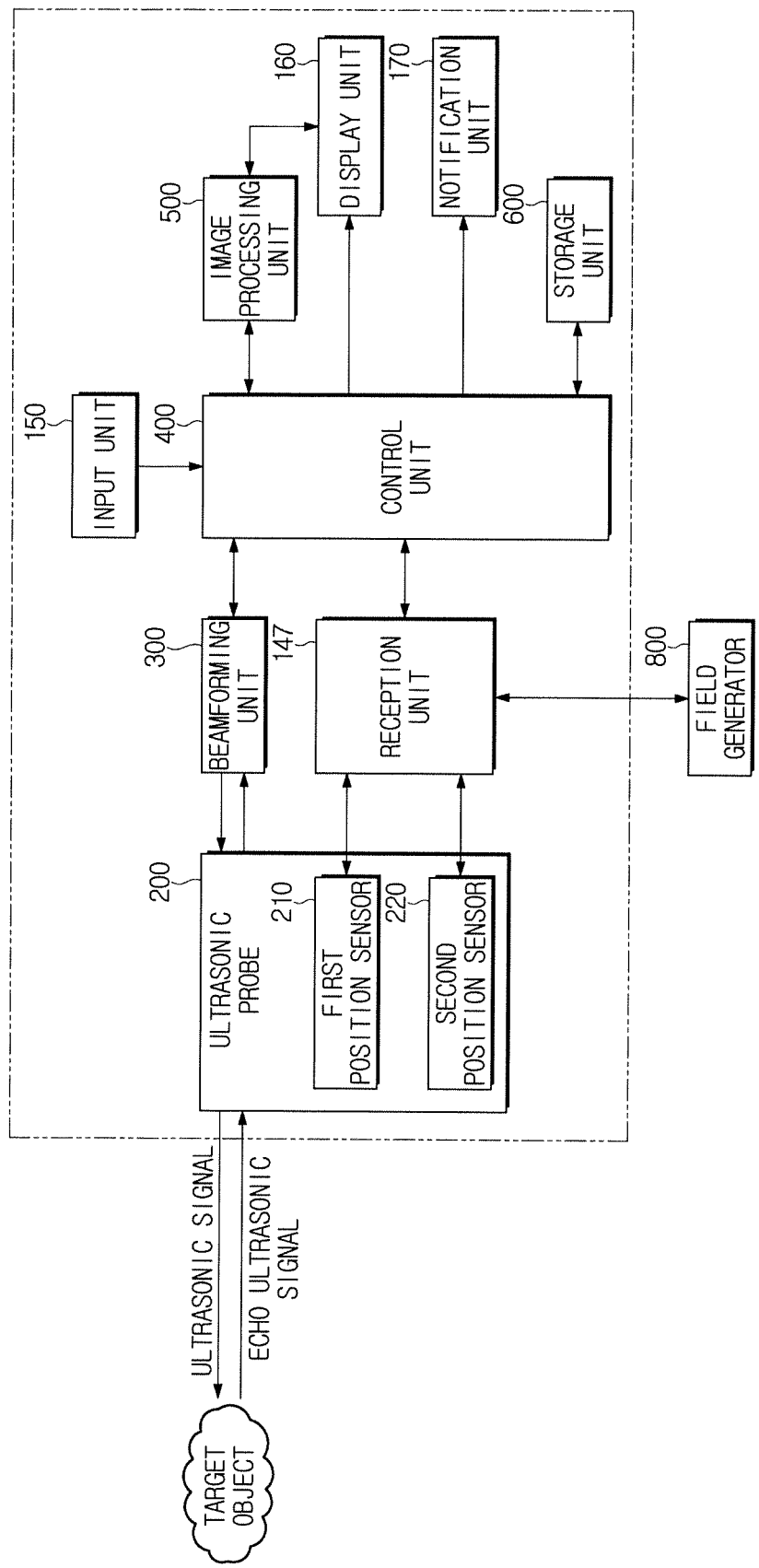
FIG. 4 is a block diagram illustrating an ultrasonic imaging apparatus according to an embodiment of the present disclosure.

FIG. 4 is a block diagram illustrating an ultrasonic imaging apparatus according to an embodiment of the present disclosure.

Referring to FIG. 4, the ultrasonic imaging apparatus 100 may include an input unit 150, a display unit 160, a notification unit 170, an ultrasonic probe 200, a beamforming unit 300, a control unit 400, an image processing unit 500, a storage unit 600, and a reception unit 147.

The ultrasonic probe 200 may be implemented in various ways within a technical idea for obtaining volume data of the target object. The ultrasonic probe 200 contacting the skin of the target object may transmit and receive ultrasonic signals to and from the target object. In more detail, the ultrasonic probe 200 may generate ultrasonic signals according to input pulses, transmit the generated ultrasonic signals to the target object, and receive echo ultrasonic signals reflected from a specific part contained in the target object. In addition, the ultrasonic probe 200 may establish the position for medical image matching, and may establish the position for medical image matching by moving the ultrasonic probe 200 toward the target object. In this case, the position setting for medical image setting may be established based on the coordinate information obtained by several position sensors mounted to the ultrasonic probe 200.

The first position sensor 210 and the second position sensor 220 spaced apart from each other by a predetermined distance may be mounted to the ultrasonic probe 200. Position information of the ultrasonic probe 200 may be obtained. Although only one position sensor may be mounted to the ultrasonic probe 200, it is more preferable that two or more position sensors may be mounted to the ultrasonic probe 200 so as to acquire more correct position information.

The first position sensor 210 and the second position sensor 220 may obtain position information of the ultrasonic probe 200 on the basis of spatial coordinate information thereof. Spatial coordinate information of the first and second position sensors (210, 220) may be determined on the basis of the position of the field generator 800. That is, if the position of the field generator 800 is used as a reference point, the separation direction and distance in spatial coordinates between the first position sensor 210 and the second position sensor 220 may be determined on the basis of signals generated from the field generator 800, such that coordinate information of the first position sensor 210 and the second position sensor 220 may be determined. That is, distance information and direction information of the first position sensor 210 and the second position sensor 220 on the basis of the position of the field generator 800 may be contained in coordinate information of the first position sensor 210 and the second position sensor 220.

Distance information of the first position sensor 210 and the second position sensor 220 may include information regarding a separation distance between the field generator 800 and each of the first and second position sensors (210, 220) when the first and second position sensors (210, 220) move in the space, and may further include information regarding a separation distance between the first position sensor 210 and the second position sensor 220.

In addition, information regarding the direction of the first and second position sensors (210, 220) may include specific information indicating the direction and position of the first and second position sensors (210, 220) moving in the space on the basis of the position of the field generator 800, and may further include information regarding the mutual direction between the first position sensor 210 and the second position sensor 220.

In other words, coordinate information of the first position sensor 210 and the second position sensor 220 may include the direction and distance of each position sensor on the basis of the position of the field generator 800, wherein the direction and distance form a vector, such that the direction and distance vector may be stored in the storage unit 600.

The first position sensor 210 and the second position sensor 220 may transmit output signals, and the output signals may be converted into coordinate information in association with the relationship between the above output signals and other output signals of the field generator 800, and then transmitted to the reception unit 147.

The reception unit 147 may receive output signals from the first position sensor 210, the second position sensor 220, and the field generator 800, and may transmit the received output signals to the control unit 400. In addition, the reception unit 147 may receive the determined coordinate information of the first position sensor 210 and the second position sensor 220 on the basis of output signals of the field generator 800, and may transmit the received information to the control unit 400.

The beamforming unit 300 may perform beamforming to focus ultrasonic signals transmitted/received to/from the ultrasonic probe 200. The beamforming unit 300 includes a transmit (Tx) beamformer (not shown) and a receive (Rx) beamformer (not shown), such that analog signals can be converted into digital signals and vice versa, and a time difference between ultrasonic signals transmitted from at least one transducer and ultrasonic signals received from at least one transducer can be adjusted. The beamforming unit 300 may be contained in the main body 100 of the ultrasonic imaging apparatus 100 as shown in FIG. 1, or may be embedded in the ultrasonic probe 200 such that a unique function thereof can be carried out. If the ultrasonic probe is a wireless probe connected to the ultrasonic imaging apparatus 100 through a wireless communication network, the beamforming unit 300 may be contained in the wireless communication probe. The beamforming unit 300 may implement any of various beamforming methods well known to those skilled in the art, a combination of several beamforming methods may be applied to the beamforming unit 300, or any one of the beamforming methods may be selectively applied thereto.

The control unit 400 may receive beamforming data from the beamforming unit 300, and may transmit data in a manner that the image processing unit 500 can perform image processing.

The control unit 400 may calculate a first distance between the field generator 800 and the first position sensor 210 on the basis of coordinate information of the first position sensor 210 mounted to the ultrasonic probe 200, and may calculate a second distance between the field generator 800 and the second position sensor 220 on the basis of coordinate information of the second position sensor 220 mounted to the ultrasonic probe 200. The control unit 400 may determine the direction of the first position sensor 210 and the direction of the second position sensor 220 on the basis of the position of the field generator 800.

In addition, the control unit 400 may calculate the distance between the first position sensor 210 and the second position sensor 220 on the basis of coordinate information of the first position sensor 210 and coordinate information of the second position sensor 220, and may compare the calculated distance between the first position sensor 210 and the second position sensor 220 with a predetermined distance. Further, the control unit 400 may compare information regarding the mutual direction between the first position sensor 210 and the second position sensor 220 with predetermined direction information.

That is, the control unit 400 may calculate the distance between the first position sensor 210 and the second position sensor 220, may compare the calculated distance with the stored distance information between the first position sensor 210 and the second position sensor 220, and may determine whether at least one of the first position sensor 210 and the second position sensor 220 is separated from the ultrasonic probe 200. In addition, the control unit 400 may recognize a difference in direction between the second position sensor 220's direction information and the stored direction information on the basis of the position of the first position sensor 210, and may also recognize a difference in direction between the first position sensor 210's direction information and the stored direction information on the basis of the position of the second position sensor 220.

In more detail, assuming that the distance between the first position sensor 210 and the second position sensor 220 is shorter or longer than the prestored distance, this means that at least one of the first position sensor 210 and the second position sensor 220 is separated from the ultrasonic probe 200. In this case, the first position sensor 210's direction information and the second position sensor 220's direction information may be used as auxiliary indices for determining the separation or non-separation of the first position sensor 210 and the second position sensor 220.

The control unit 400 may compare strengths of signals received from the first position sensor 210 and the second position sensor 220 with the predetermined signal strength, and may also determine that one position sensor having lower signal strength is separated from the ultrasonic probe 200 according to the comparison result. In addition, the control unit 400 may compare strengths of signals, and thus determine the presence or absence of a peripheral obstacle in the peripheral region of the position sensor having lower signal strength according to the comparison result.

The control unit 400 may be implemented as an array composed of a plurality of logical gates, and may also be implemented as a combination of a universal microprocessor and a memory storing programs capable of being executed in the universal microprocessor.

The image processing unit 500 may generate an ultrasonic image by processing the beamformed echo ultrasonic signals. The image processing unit 500 may process the echo ultrasonic signals using any well-known image processing methods. For example, the image processing unit 500 may perform time gain compensation (TGC) processing of the beamformed echo ultrasonic signals. Thereafter, the image processing unit 500 may establish a dynamic range (DR). After the DR is established, the image processing unit 500 may compress the echo ultrasonic signals belonging to the DR. Finally, the image processing unit 500 rectifies the echo ultrasonic signals, and thus removes noise from the rectified ultrasonic signals. The image processing unit 500 may generate an ultrasonic image using the processed echo ultrasonic signals. The image processing unit 500 may generate various kinds of ultrasonic images. For example, the ultrasonic images generated by the image processing unit 500 may include an A-mode (Amplitude Mode) image, a B-mode (Brightness Mode) image, an M-mode (Motion Mode) image, and a Doppler mode image.

In addition, the image processing unit 500 may generate image data for informing the user that at least one of the first position sensor 210 and the second position sensor 220 is separated from the ultrasonic probe 200 under control of the control unit 400. The generated image data may be transferred to the display unit 160, and the display unit 160 may display specific information indicating whether at least one of the first position sensor 210 and the second position sensor 220 is separated from the ultrasonic probe 200. In addition, the display unit 160 may also display strengths of signals generated from the first position sensor 210 and the second position sensor 220.

If the control unit 400 determines that at least one of the first position sensor 210 and the second position sensor 220 is separated from the ultrasonic probe 200, the notification unit 170 may audibly inform the user of specific information indicating whether at least one of the first position sensor 210 and the second position sensor 220 is separated from the ultrasonic probe under control of the control unit 400. That is, the notification unit 170 outputs a voice signal or predetermined warning sound, such that it can inform the user of separation or non-separation of at least one of the first position sensor 210 and the second position sensor 220.

The storage unit 600 may store strength of the field generator 800's signal received by the reception unit 147 and strength of output signals of the first position sensor 210 and the second position sensor 220, and may store the first position sensor 210's coordinate information and the second position sensor 220's coordinate information that are determined on the basis of the output signal of the field generator 800.

The storage unit 600 may store information regarding the distance between the first position sensor 210 and the second position sensor 220 mounted to the ultrasonic probe 200, and may also store strength information of signals generated from the first position sensor 210 and the second position sensor 220 that are not separated from the ultrasonic probe 200.

For example, although the storage unit 600 may include a high-speed random access memory (RAM), a magnetic disc, an SRAM, a DRAM, a ROM, etc., the scope or spirit of the present disclosure is not limited thereto. In addition, the storage unit 600 may be detachably coupled to the ultrasonic imaging apparatus 100. For example, although the storage unit 600 may include a Compact Flash (CF) card, a Secure Digital (SD) card, a Smart Media (SM) card, a Multimedia Card (MMC), or a memory stick, the scope or spirit of the present disclosure is not limited thereto. In addition, the storage unit 600 is located outside the ultrasonic imaging apparatus 100, and may transmit or receive data to or from the ultrasonic imaging apparatus 100 by wire or wirelessly.

As shown in FIG. 1, the input unit 150 may input a control command for the ultrasonic imaging apparatus 100 or a control command for one constituent element contained in the ultrasonic imaging apparatus 100, and may also input a control command for medical image matching. In addition, the input unit 150 may input data for implementing the above-mentioned ultrasonic imaging apparatus and the method for controlling the same, and may store the data in the storage unit 600. Redundant matters will not be described herein for clarity.

The display unit 160 may display various UIs related to overall control of the ultrasonic imaging apparatus 100, and may display ultrasonic images obtained from the ultrasonic diagnosis procedure. If the medical image matching is achieved, the display unit 160 may display the matched medical image. The display unit 160 may display specific information indicating whether at least one of the first position sensor 210 and the second position sensor 220 is separated from the ultrasonic probe 200, and may display the change of signal strengths of the first position sensor 210 and the second position sensor 220.

Figure 5:
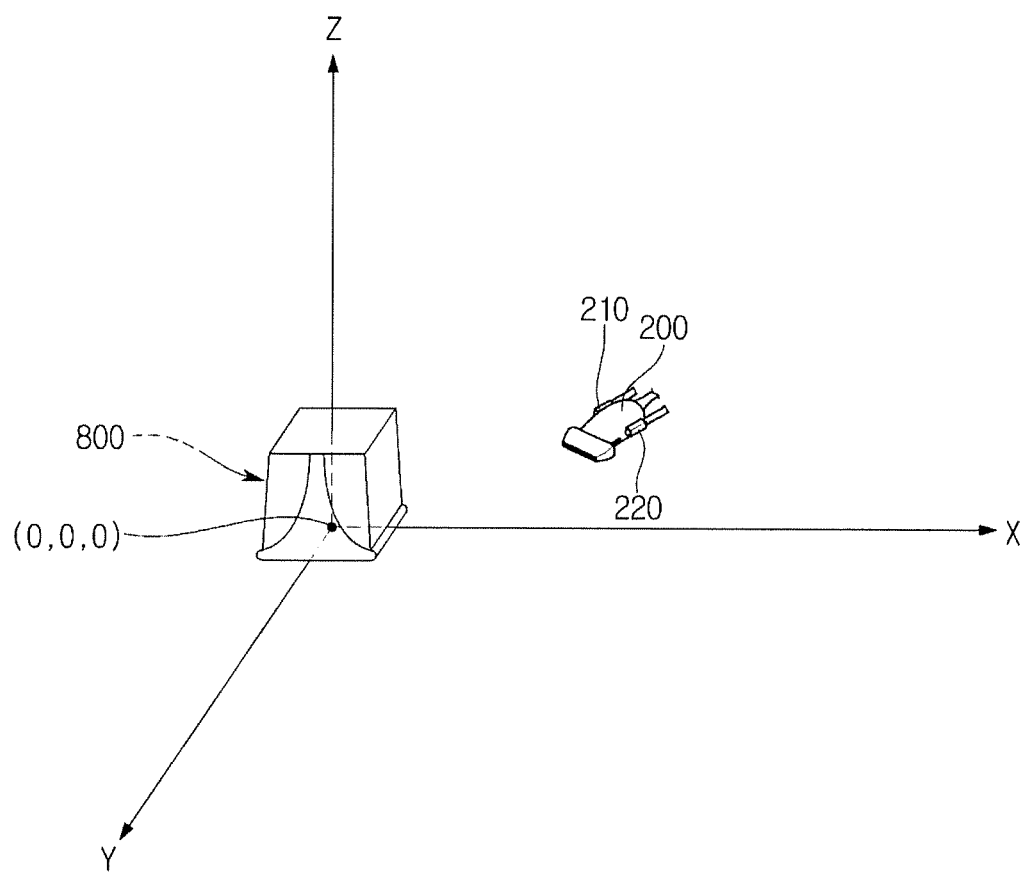
FIG. 5 is a conceptual diagram illustrating a method for determining coordinate information of the position sensor according to an embodiment of the present disclosure.

FIG. 5 is a conceptual diagram illustrating a method for determining coordinate information of the position sensor according to an embodiment of the present disclosure.

Referring to FIG. 5, coordinate information of the first position sensor 210 and the second position sensor 220 mounted to the ultrasonic probe 200 may include information regarding the position of the ultrasonic probe 200 in the coordinate system determined on the basis of the position of the field generator 800. That is, position information of the ultrasonic probe 200 may include information regarding at least one of the direction, slope, and rotation angle of the ultrasonic probe 200 in the space. The position information of the ultrasonic probe 200 may be acquired as the coordinate information of the first and second position sensors (210, 220) mounted to the ultrasonic probe 200.

Although not shown in the drawings, another position sensor located at the target object may be present, and the control unit 400 may calculate the distance between the first position sensor 210 and the second position sensor 220 on the basis of coordinate information between the position sensor located at the target object and each of the first position sensor 210 and the second position sensor 220.

The coordinate information of the first position sensor 210 and the second position sensor 220 will hereinafter be described on the basis of a coordinate system (hereinafter referred to as a DICOM coordinate system) used by DICOM (Digital Imaging and Communication in Medicine) standard.

Referring to FIG. 5, the field generator 800 may be used as a reference point for determining 3D spatial coordinate information of the first and second position sensors (210, 220). That is, assuming that the field generator 800 corresponds to the start point (0, 0, 0) in the spatial coordinate system, the first position sensor 210 and the second position sensor 220 may be spaced apart from the start point by a predetermined distance in the spatial coordinate system, and the coordinate information may be determined on the basis of output signals of the first position sensor 210 and the second position sensor 220.

Coordinate information of the first position sensor 210 and the second position sensor 220 may include distance and direction information of the first position sensor 210 and the second position sensor 220 on the basis of the position of the field generator 800. That is, coordinate information of the first position sensor 210 and the second position sensor 220 may be denoted by vectors, such that specific information indicating how far each position sensor is spaced apart from the field generator 800 and also indicating directivity of each position sensor on the basis of the position of the field generator 800 can be determined.

The field generator 800 is located at other coordinates instead of the start point of the spatial coordinates, and the reception unit 147 of the ultrasonic imaging apparatus 100 can receive the output signal of the field generator 800 and the output signals of the first and second position sensors (210, 220), such that coordinate information of the first position sensor 210 and the second position sensor 220 may be determined on the basis of the position of the field generator 800.

If the user moves the ultrasonic probe 200, spatial coordinate information of the first and second position sensors (210, 220) may be changed on the basis of the position of the field generator 800. That is, although (x, y, z) coordinates of the first position sensor 210 may be changed in real time and (x, y, z) coordinates of the second position sensor 220 may be changed in real time, the distance between the first position sensor 210 and the second position sensor 220 may remain constant. For example, assuming that the distance between the first position sensor 210 and the second position sensor 220 is denoted by 'S', coordinates of the first position sensor 210 are denoted by $(x_1, y_1, z_1)$, and coordinates of the second position sensor 220 are denoted by $(x_2, y_2, z_2)$, the distance between the first position sensor 210 and the second position sensor 220 may be represented by the following equation 1.

$$S=\sqrt{(x_1-x_2)^2+(y_1-y_2)^2+(z_1-z_2)^2} \quad \text{[Equation 1]}$$

Since the field generator 800, the first position sensor 210, and the second position sensor 220 are coupled to the reception unit 147, the reception unit 147 may receive the determined coordinate information of the first and second position sensors (210, 220) on the basis of the output signal of the field generator 800, and may transmit the received coordinate information to the control unit 400.

Figure 6:
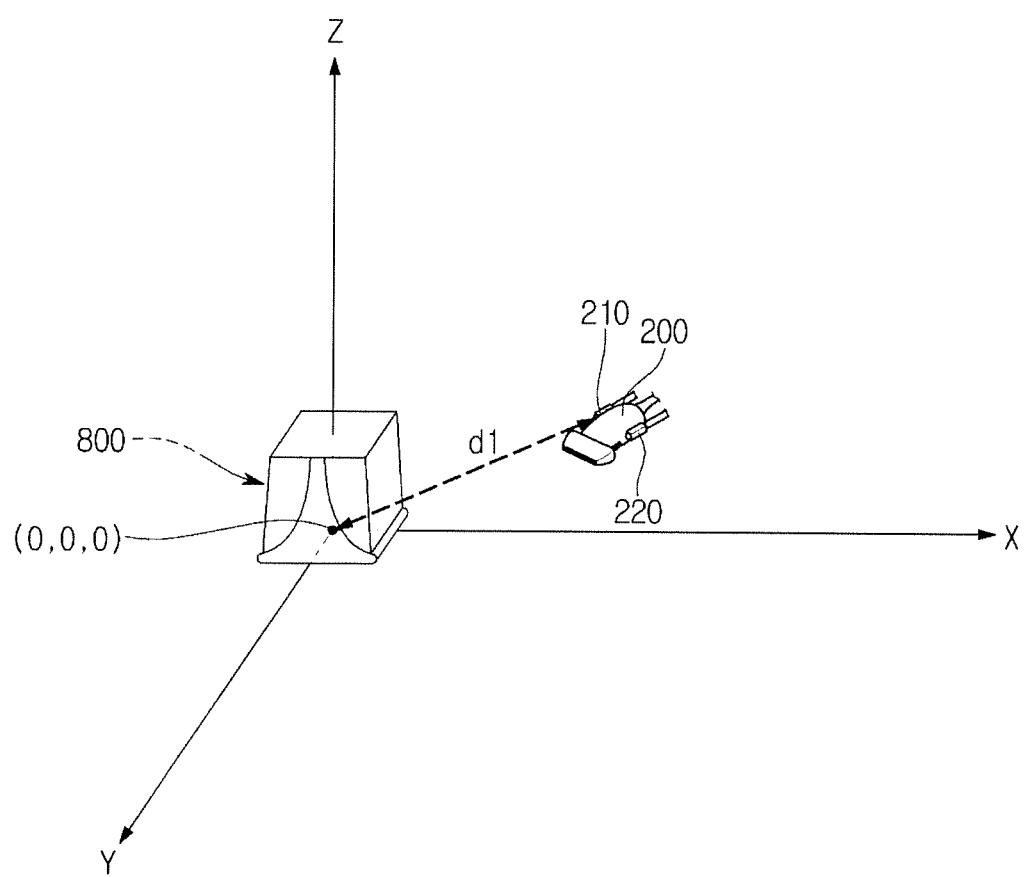
FIG. 6 is a conceptual diagram illustrating a method for calculating a distance between a field generator and a first position sensor according to an embodiment of the present disclosure.
Figure 7:
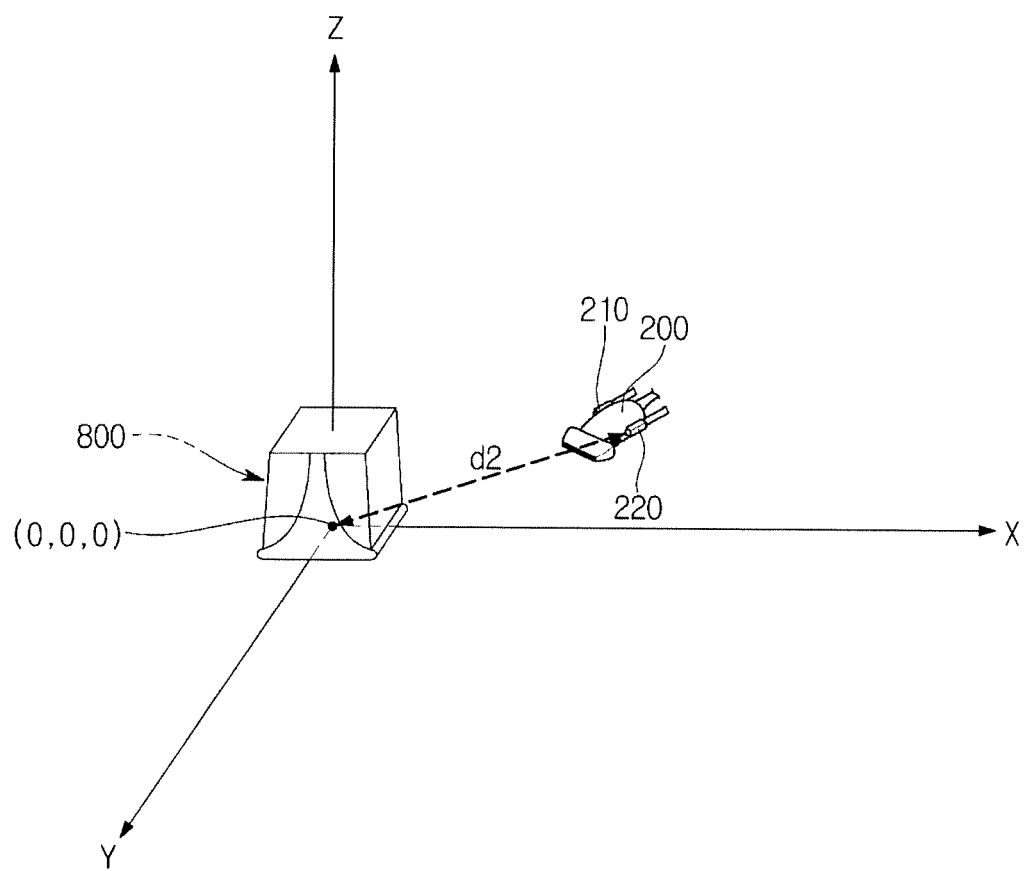
FIG. 7 is a conceptual diagram illustrating a method for calculating a distance between a field generator and a second position sensor according to an embodiment of the present disclosure.
Figure 8:
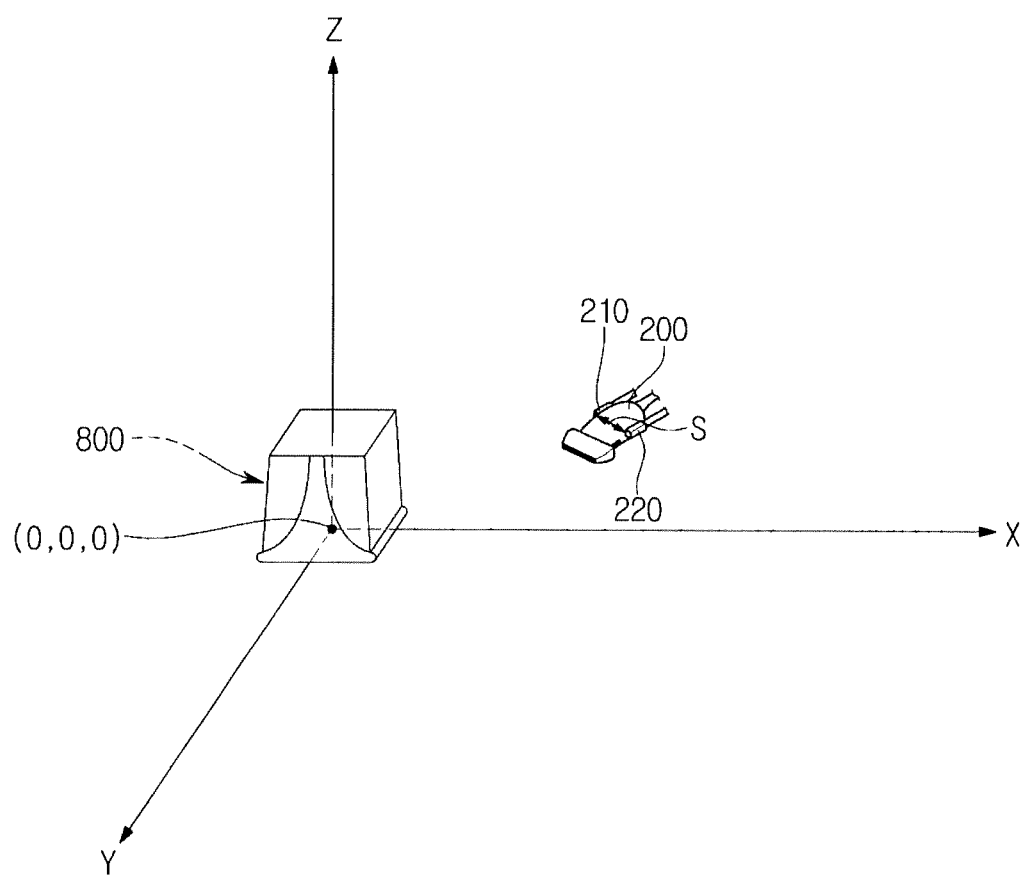
FIG. 8 is a conceptual diagram illustrating a method for calculating a distance between a first position sensor and a second position sensor according to an embodiment of the present disclosure.

FIG. 6 is a conceptual diagram illustrating a method for calculating a distance between a field generator and a first position sensor according to an embodiment of the present disclosure. FIG. 7 is a conceptual diagram illustrating a method for calculating a distance between a field generator and a second position sensor according to an embodiment of the present disclosure. FIG. 8 is a conceptual diagram illustrating a method for calculating a distance between a first position sensor and a second position sensor according to an embodiment of the present disclosure.

Referring to FIG. 6, the control unit 400 may calculate the distance between the field generator 800 and the first position sensor 210 on the basis of the coordinate information of the first position sensor 210.

As described above, assuming that the field generator 800 is located at the start point (origin) of the spatial coordinates, the first position sensor 210 may be located at the space spaced apart from the start point (origin) by a predetermined distance, and the coordinate information of the first position sensor 210 may be determined on the basis of the position of the field generator 800. If the field generator 800 is located at an arbitrary point but not the start point, coordinate information of the first position sensor 210 may be determined on the basis of the arbitrary point.

The control unit 400 may receive the output signal of the field generator 800 through the reception unit 147, and may calculate a linear distance between the field generator 800 and the first position sensor 210 on the basis of the determined coordinate information of the first position sensor 210 depending upon the output signal of the field generator 800. Assuming that the linear distance calculated by the control unit 400 is denoted by 'd1', and the coordinates of the field generator 800 are denoted by $(x_0, y_0, z_0)$ and the coordinates of the first position sensor 210 are denoted by $(x_1, y_1, z_1)$, the linear distance (d1) may be calculated using the following equation 2.

$$d1=\sqrt{(x_1-x_0)^2+(y_1-y_0)^2+(z_1-z_0)^2} \quad \text{[Equation 2]}$$

Since the coordinate information of the first position sensor 210 includes position information of the ultrasonic probe 200, the medical image matching position for the target object may be determined on the basis of the determined coordinate information of the first position sensor 210 based on the position of the field generator 800.

In addition, since the coordinate information of the first position sensor 210 includes direction information of the ultrasonic probe 200 on the basis of the position of the field generator 800, the direction of the first position sensor 210 may be determined according to movement of the ultrasonic probe 200.

If the user moves the ultrasonic probe 200, spatial coordinate information of the first position sensor 210 may be changed in real time on the basis of the position of the field generator 800, such that the control unit 400 may calculate the distance (d1) between the field generator 800 and the first position sensor 210, may detect the direction of the first position sensor 210, and may recognize, in real time, position information of the ultrasonic probe 200 for medical image matching.

Referring to FIG. 7, the control unit 400 may calculate the distance between the field generator 800 and the second position sensor 220 on the basis of coordinate information of the second position sensor 220.

As described above, assuming that the field generator 800 is located at the start point (origin) of the spatial coordinates, the second position sensor 220 may be located at the space spaced apart from the start point (origin) by a predetermined distance, and the coordinate information of the second position sensor 220 may be determined on the basis of the position of the field generator 800. If the field generator 800 is located at an arbitrary point but not the start point, coordinate information of the second position sensor 220 may be determined on the basis of the arbitrary point.

The control unit 400 may receive the output signal of the field generator 800 through the reception unit 147, and may calculate a linear distance between the field generator 800 and the second position sensor 220 on the basis of the determined coordinate information of the second position sensor 220 depending upon the output signal of the field generator 800. Assuming that the linear distance calculated by the control unit 400 is denoted by 'd2', and the coordinates of the field generator 800 are denoted by $(x_0, y_0, z_0)$ and the coordinates of the second position sensor 220 are denoted by $(x_2, y_2, z_2)$, the linear distance (d2) may be calculated using the following equation 3.

$$d2=\sqrt{(x_2-x_0)^2+(y_2-y_0)^2+(z_2-z_0)^2} \quad \text{[Equation 3]}$$

Since the coordinate information of the second position sensor 220 includes position information of the ultrasonic probe 200, the medical image matching position for the target object may be determined on the basis of the determined coordinate information of the second position sensor 220 based on the position of the field generator 800.

In addition, since the coordinate information of the second position sensor 220 includes direction information of the ultrasonic probe 200 on the basis of the position of the field generator 800, the direction of the second position sensor 220 may be determined according to movement of the ultrasonic probe 200.

If the user moves the ultrasonic probe 200, spatial coordinate information of the second position sensor 220 may be changed in real time on the basis of the position of the field generator 800, such that the control unit 400 may calculate the distance (d2) between the field generator 800 and the second position sensor 220, may detect the direction of the second position sensor 220, and may recognize, in real time, position information of the ultrasonic probe 200 for medical image matching.

Referring to FIG. 8, the control unit 400 may calculate the distance between the first position sensor 210 and the second position sensor 220 on the basis of coordinate information of the first position sensor 210 and the second position sensor 220.

As described above, assuming that the field generator 800 is located at the start point (origin) of the spatial coordinates, the first and second position sensors (210, 220) may be located at the space spaced apart from the start point (origin) by a predetermined distance, and the coordinate information of the first and second position sensors (210, 220) may be determined on the basis of the position of the field generator 800. If the field generator 800 is located at an arbitrary point but not the start point, coordinate information of the first and second position sensors (210, 220) may be determined on the basis of the arbitrary point.

The control unit 400 may receive the output signal of the field generator 800 through the reception unit 147, and may calculate a linear distance between the first position sensor 210 and the second position sensor 220 on the basis of the determined coordinate information of the first and second position sensors (210, 220) depending upon the output signal of the field generator 800.

Assuming that the linear distance between the first position sensor 210 and the second position sensor 220 is denoted by S, and the coordinates of the first position sensor 210 are denoted by $(x_1, y_1, z_1)$ and the coordinates of the second position sensor 220 are denoted by $(x_2, y_2, z_2)$, the distance (S) between the first position sensor 210 and the second position sensor 220 may be calculated by the following equation 1 shown in FIG. 5.

Since the coordinate information of the first and second position sensors (210, 220) includes position information of the ultrasonic probe 200, the medical image matching position for the target object may be determined on the basis of the determined coordinate information of the first and second position sensors (210, 220) based on the position of the field generator 800.

In addition, since the coordinate information of the first and second position sensors (210, 220) includes direction information of the ultrasonic probe 200 on the basis of the position of the field generator 800, the direction of the first and second position sensors (210, 220) may be determined according to movement of the ultrasonic probe 200.

If the user moves the ultrasonic probe 200, spatial coordinate information of the first and second position sensors (210, 220) may be changed in real time on the basis of the position of the field generator 800, such that the control unit 400 may calculate the distance (S) between the first position sensor 210 and the second position sensor 220, may detect the directions of the first and second position sensors (210, 220), and may recognize, in real time, position information of the ultrasonic probe 200 for medical image matching.

Figure 9:
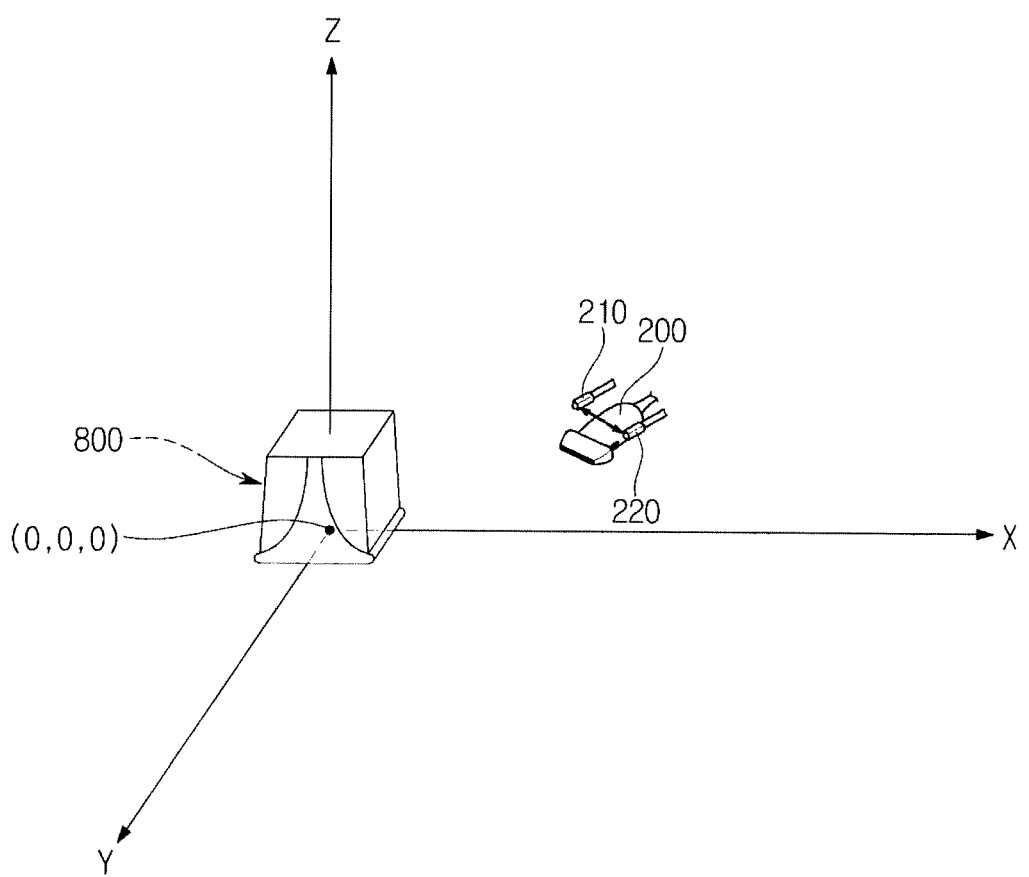
FIG. 9 is a conceptual diagram illustrating a method for determining whether at least one of the first position sensor and the second position sensor is separated from an ultrasonic probe according to an embodiment of the present disclosure.

FIG. 9 is a conceptual diagram illustrating a method for determining whether at least one of the first position sensor and the second position sensor is separated from an ultrasonic probe according to an embodiment of the present disclosure.

As can be seen from FIG. 8, the control unit 400 may calculate a predetermined distance between the first position sensor 210 and the second position sensor 220 on the basis of coordinate information of the first and second position sensors (210, 220), and may compare the calculated distance with a predetermined distance. In this case, the predetermined distance between the first position sensor 210 and the second position sensor 220 may be data of the distance (S) between the first position sensor 210 and the second position sensor 220 on the assumption that the first and second position sensors (210, 220) are mounted to the ultrasonic probe 200 as shown in FIG. 8.

The distance (S) data between the first position sensor 210 and the second position sensor 220 may be stored in the storage unit 600. Even when the user moves the ultrasonic probe 200, if at least one of the first position sensor 210 and the second position sensor 220 is not separated from the ultrasonic probe 200, the distance (S) between the first position sensor 210 and the second position sensor 220 remains unchanged.

However, if at least one of the first position sensor 210 and the second position sensor 220 is separated from the ultrasonic probe, the distance between the first position sensor 210 and the second position sensor 220 may be different from the predetermined distance (S).

While the user changes the position of the ultrasonic probe 200 in real time, the control unit 400 may calculate, in real time, the distance between the first position sensor 210 and the second position sensor 220 can be calculated on the basis of the first and second position sensors (210, 220)' coordinate information that has been obtained by the reception unit 147 and then applied to the control unit 400, and may compare the calculated distance with the distance information stored in the storage unit 600.

If the realtime-calculated distance between the first position sensor 210 and the second position sensor 220 is different from the prestored distance, the control unit 400 may determine that at least one of the first position sensor 210 and the second position sensor 220 is separated from the ultrasonic probe 200. That is, if the distance between the first position sensor 210 and the second position sensor 220 is shorter or longer than the prestored distance, the control unit 400 may determine that at least one of the first position sensor 210 and the second position sensor 200 is separated from the ultrasonic probe 200.

As described above, since the coordinate information of the first and second position sensors (210, 220) includes not only the distance information between the first position sensor 210 and the second position sensor 220, but also the direction information of the first and second position sensors (210, 220), the control unit 400 may determine that at least one of the first and second position sensors (210, 220) is separated from the ultrasonic probe 200 even when the distance and direction of each position sensor are simultaneously changed.

FIG. 9 exemplarily discloses that the first position sensor 210 is separated from the ultrasonic probe 200. When the first position sensor 210 is separated from the ultrasonic probe 200 as shown in FIG. 9, the distance between the first position sensor 210 and the second position sensor 220 may be longer than the predetermined distance and the directions of the first and second position sensors (210, 22) may be different from the predetermined directions.

As described above, when at least one of the first position sensor 210 and the second position sensor 220 is separated from the ultrasonic probe 200, it is impossible to correctly establish the position of the ultrasonic probe 200 for medical image matching, such that it is necessary to perform the medical image matching by establishing the correct position of the ultrasonic probe 200.

Figure 10:
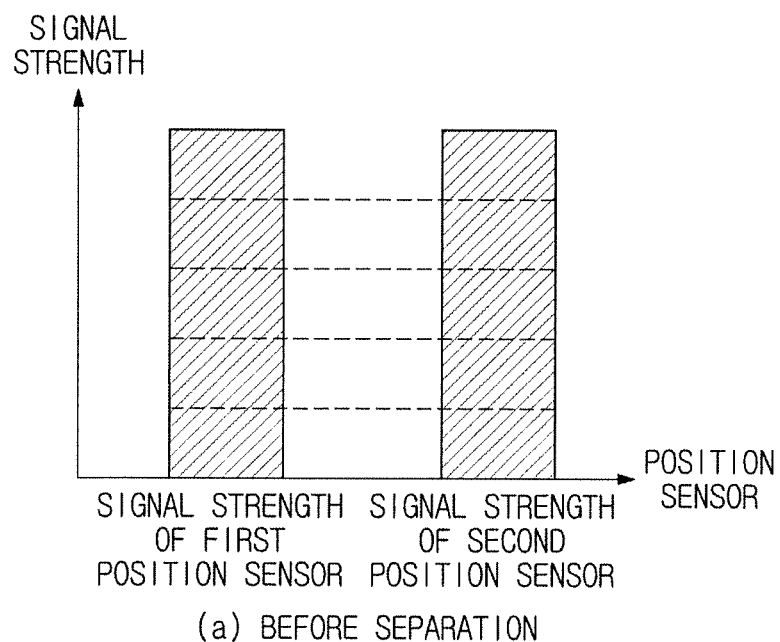
FIG. 10 is a conceptual diagram illustrating a method for determining strength of signals generated from the first position sensor and the second position sensor according to an embodiment of the present disclosure.
Figure 10:
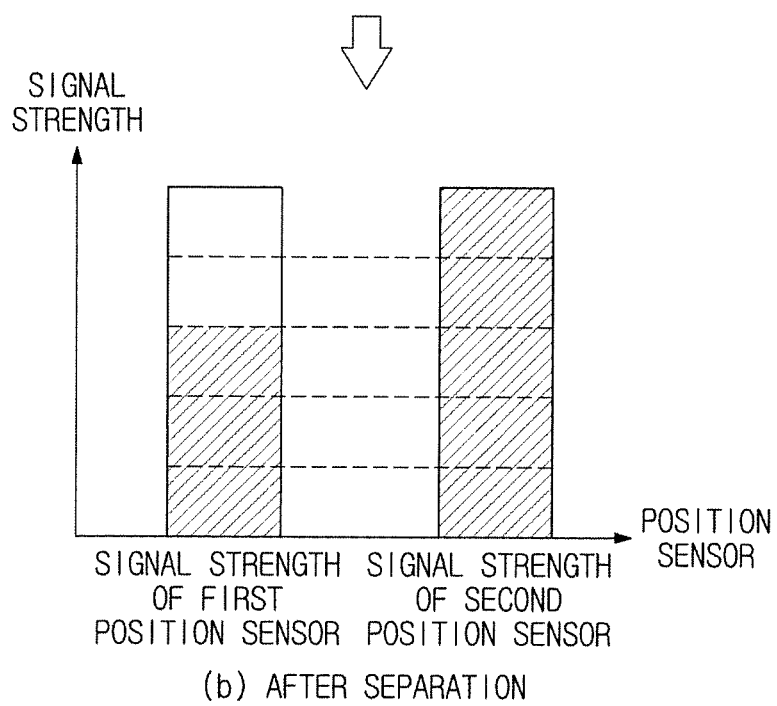

FIG. 10 is a conceptual diagram illustrating a method for determining strength of signals generated from the first position sensor and the second position sensor according to an embodiment of the present disclosure.

As described above, signals can be transmitted during the operation of the first and second position sensors (210, 220) mounted to the ultrasonic probe 200, and the transmitted signals can be received by the reception unit 147 and then transmitted to the control unit 400. The reception unit 147 may receive output signals of the field generator 800, and may receive strength of the signal generated between the field generator 800 and the first position sensor 210 or strength of the signal generated between the field generator 800 and the second position sensor 220.

The control unit 400 may receive strength of the output signal of each of the field generator 800, the first position sensor 210, and the second position sensor 220 from the reception unit 147, and may also receive strength of the signal generated between the field generator 800 and the first position sensor 210 and strength of the signal generated between the field generator 800 and the second position sensor 220.

The control unit 400 may compare strengths of the signals received from the first and second position sensors (210, 220), strength of the signal generated between the field generator 800 and the first position sensor 210, and strength of the signal generated between the field generator 800 and the second position sensor 220 with predetermined signal strength. In other words, the control unit 400 may compare strength of signals received from the reception unit 147 with a reference value of the signal strength stored in the storage unit 600. If the received signal strength is lower than the stored signal strength, the control unit 400 may determine that at least one of the first position sensor 210 and the second position sensor 220 is separated from the ultrasonic probe 200.

In a first case in which at least one of the first position sensor 210 and the second position sensor 220 is separated from the ultrasonic probe 200, signal strength between the field generator 800 and the first position sensor 210 or signal strength between the field generator 800 and the second position sensor 220 may be lower than a reference signal strength obtained in a second case in which at least one of the first and second position sensors (210, 220) is not separated from the ultrasonic probe 200. In addition, if at least one of the first and second position sensors (210, 220) is separated from the ultrasonic probe 200, strength of the signal generated from the separated position sensor may also be lower than a reference strength obtained in the above second case.

Therefore, the control unit 400 may determine whether at least one of the first and second position sensors (210, 220) is separated from the ultrasonic probe 200 on the basis of the distance between the first position sensor 210 and the second position sensor 220, and may also determine whether at least one of the first and second position sensors (210, 220) is separated from the ultrasonic probe 200 on the basis of strength of signals received from the field generator 800 and the plural position sensors (210, 220).

In addition, reduction of signal strength of the first position sensor 210 or the second position sensor 220 may be caused by the obstacle present in the peripheral region of the ultrasonic probe 200 or the peripheral environment of the ultrasonic probe 200. In other words, if the object configured to affect a magnetic field is present in the peripheral region of the first or second position sensor 210 or 220, the output signal of the position sensor may be reduced in strength. Since the first position sensor 210 and the second position sensor 220 correspond to the magnetic sensors, if the object affecting the magnetic field is located close to the first position sensor 210 or the second position sensor 220, the output signal of the closer position sensor may be reduced in strength.

Signal strength of the position sensor may be reduced not only by the object affecting the magnetic field, but also by the measurement environment of the space in which the ultrasonic probe 200 is located. Therefore, the control unit 400 may determine the presence or absence of the peripheral environment and the obstacle in the peripheral region of the ultrasonic probe 200 on the basis of the output signal of the field generator 800 and the output signal of the plural position sensors (210, 220).

As described above, the control unit 400 may calculate the distance between the first position sensor 210 and the second position sensor 220, may compare the calculated distance with at least one of a predetermined distance and a predetermined direction, and may compare the strengths of signals of the field generator 800, the first position sensor 210, and the second position sensor 220 with a predetermined signal strength.

In this case, the control unit 400 may determine that the distance between the first position sensor 210 and the second position sensor 220 is different from at least one of the predetermined distance and direction. If signal strength of at least one of the first position sensor 210 and the second position sensor 220 is lower than predetermined signal strength, the control unit 400 may determine that the position sensor for generating low signal strength is separated from the ultrasonic probe 200.

In contrast, the control unit 400 determines that at least one of the distance and direction between the first position sensor 210 and the second position sensor 220 is identical to at least one of the predetermined distance and direction. If signal strength of at least one of the first position sensor 210 and the second position sensor 220 is lower than predetermined signal strength, the control unit 400 may determine the presence of an obstacle in the peripheral region of the position sensor generating low signal strength or may determine whether a factor configured to reduce the output signal strength of each position sensor is present in the measurement environment.

FIG. 10(A) illustrates first signal strength obtained before the first position sensor 210 is separated from the ultrasonic probe 200, and FIG. 10(B) illustrates second signal strength obtained after the first position sensor 210 is separated from the ultrasonic probe 200.

Referring to FIG. 10, whereas strength of the output signal of the first position sensor 210 is identical to strength of the output signal of the second position sensor 220 before the first position sensor 210 is separated from the ultrasonic probe 200, strength of the output signal of the first position sensor 210 may be lower than strength of the output signal of the second position sensor 220 because the distance between the first position sensor 210 and the ultrasonic probe 200 is relatively longer than the distance between the second position sensor 220 and the ultrasonic probe 200 when the first position sensor 210 is separated from the ultrasonic probe 200.

In addition, even when the first position sensor 210 is not separated from the ultrasonic probe 200, if the obstacle is in the peripheral region of the first position sensor 210 or if the factor causing the reduction of signal strength is in the peripheral measurement environment of the first position sensor 210, the output signal of the first position sensor 210 may be reduced in strength as shown in FIG. 10.

Figure 11:
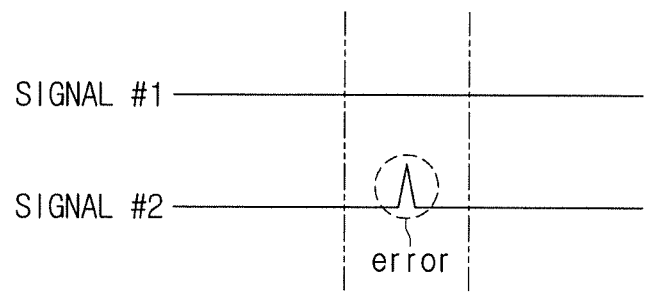
FIG. 11 is a conceptual diagram illustrating a method for correcting the occurrence of abnormal signals by reflecting information as to whether the position sensor is separated from the ultrasonic probe according to an embodiment of the present disclosure.
Figure 11:
Figure 11:
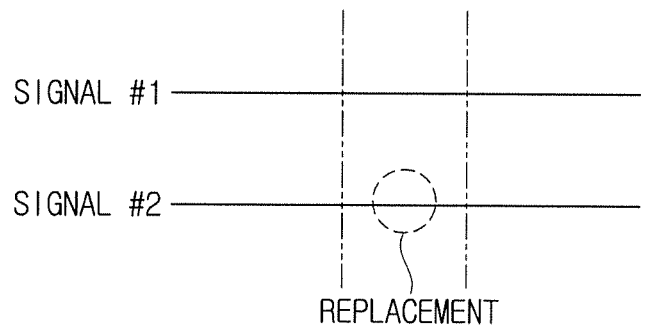

FIG. 11 is a conceptual diagram illustrating a method for correcting the occurrence of abnormal signals by reflecting information as to whether the position sensor is separated from the ultrasonic probe according to an embodiment of the present disclosure.

Referring to FIG. 11, if the first position sensor 210 and the second position sensor 220 are not separated from the ultrasonic probe 200, each position sensor 210 or 220 may transmit a predetermined or fixed signal. That is, the first position sensor 210 and the second position sensor 220 spaced apart from each other by a predetermined distance are mounted to the ultrasonic probe 200, such that the first and second position sensors (210, 220) may output similar signals in terms of shape or strength.

Referring to FIG. 11(A), whereas the output signal (hereinafter referred to as a first signal (Signal #1)) of the first position sensor 210 has a constant shape, the output signal (hereinafter referred to as a second signal (Signal #2)) of the second position sensor 220 may be instantaneously generated as irregular-shaped signals. That is, if the second position sensor 220 is separated from the ultrasonic probe 200, Signal #2 may have irregular shapes in a different way from Signal #1. Alternatively, even when a factor (e.g., obstacle) causing signal strength reduction is present in the peripheral measurement environment of the second position sensor 220, Signal #2 may also have irregular shapes.

Therefore, assuming that the control unit 400 determines that the second position sensor 220 is separated from the ultrasonic probe 200 or determines that the factor causing the signal strength reduction is present in the peripheral measurement environment of the second position sensor 220, there is a need to inform the user of the separation of the second position sensor 220 or the presence of the factor causing the signal strength reduction.

However, when the control unit 400 calculates the distance between the first position sensor 210 and the second position sensor 220, compares the calculated distance with a predetermined distance, and determines that the second position sensor 220 is not separated from the ultrasonic probe 200, and when strength of the output signal of the second position sensor 220 is identical to strength of the output signal of the first position sensor 210, irregular shapes contained in Signal #2 may indicate the occurrence of an abnormal signal (error) based on a system error.

If irregular shapes of Signal #2 are determined to be a result of system error, the control unit 400 may replace the error part of Signal #2 with some parts of Signal #1. As shown in FIG. 11(B), the error part of Signal #2 may be replaced with a normal-shaped part of Signal #1.

That is, the control unit 400 determines whether at least one of the first position sensor 210 and the second position sensor 220 is separated from the ultrasonic probe 200, determines strength of the output signal of the first or second position sensor 210 or 220, and reflects the determined result into error correction of the output signal of the first or second position sensor 210 or 220.

Figure 12:
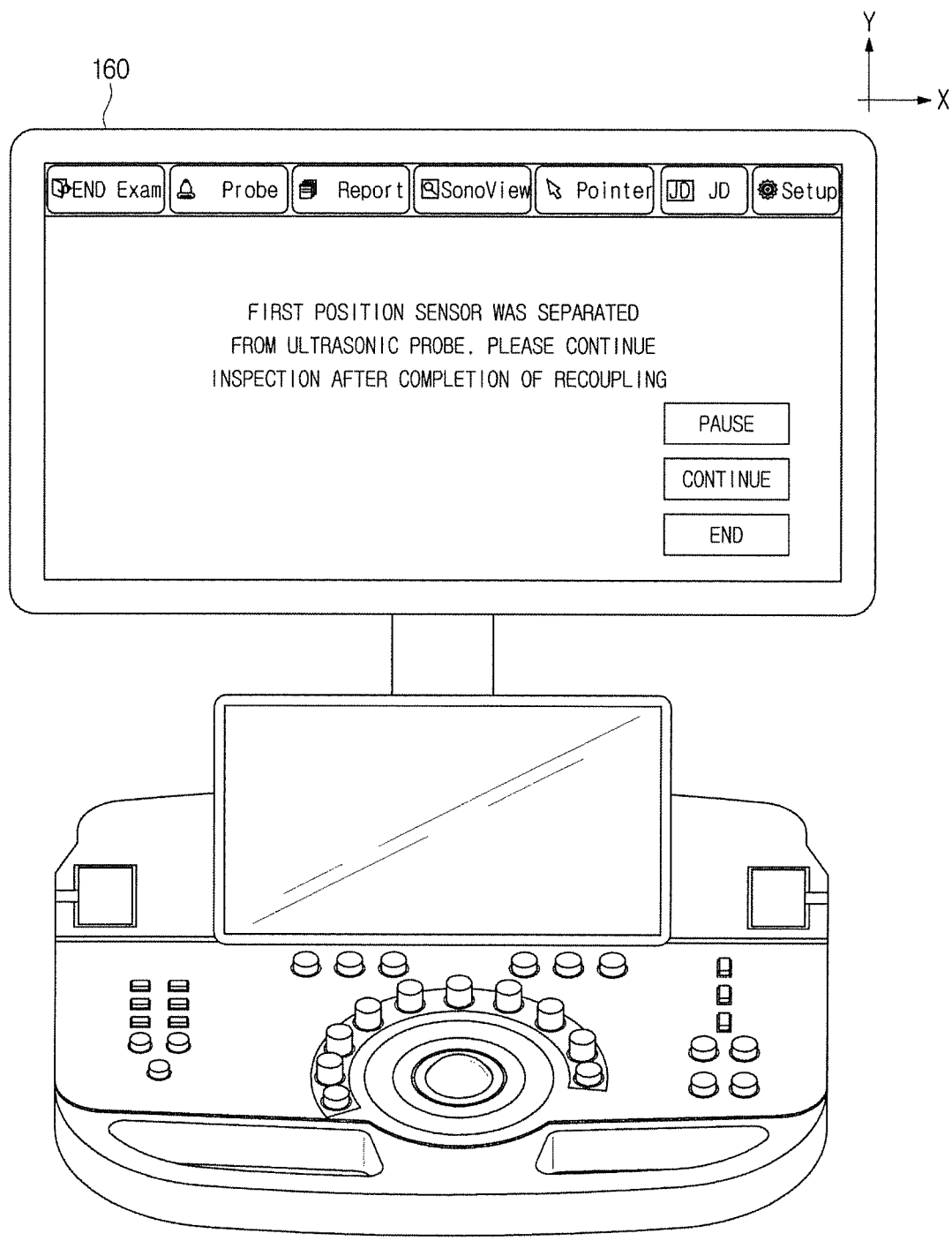
FIG. 12 is a view illustrating a display unit for displaying information indicating whether the position sensor is separated from the ultrasonic probe using letters or characters according to an embodiment of the present disclosure
Figure 13:
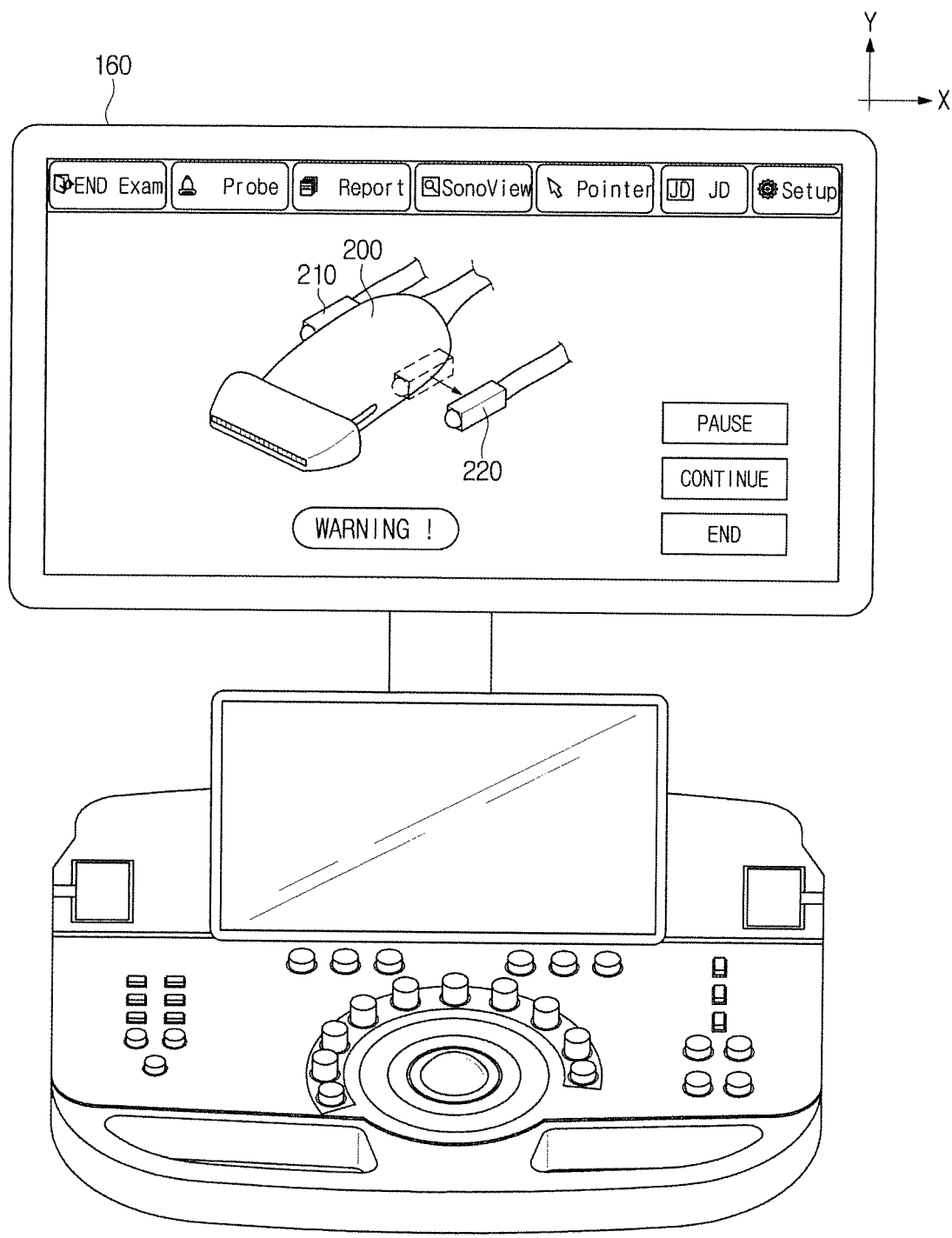
FIG. 13 is a view illustrating a display unit for displaying information indicating whether the position sensor is separated from the ultrasonic probe using pictures or drawings according to an embodiment of the present disclosure.

FIG. 12 is a view illustrating a display unit for displaying information indicating whether the position sensor is separated from the ultrasonic probe using letters or characters according to an embodiment of the present disclosure. FIG. 13 is a view illustrating a display unit for displaying information indicating whether the position sensor is separated from the ultrasonic probe using pictures or drawings according to an embodiment of the present disclosure.

As described above, the control unit 400 may determine whether at least one of the first and second position sensors (210, 220) mounted to the ultrasonic probe 200 is separated from the ultrasonic probe 200. If the at least one position sensor is separated from the ultrasonic probe 200, the control unit 400 may inform the user of the separation of the position sensor, such that the control unit 400 can prevent the prosecution of inspection on the condition that the position sensor is separated from the ultrasonic probe 200.

Therefore, the control unit 400 controls the display unit 160 such that the display unit 160 can display specific information indicating whether at least one of the first position sensor 210 and the second position sensor 220 is separated from the ultrasonic probe 200. Various methods for displaying the specific information on the display unit 160 may be used, for example, a method for graphically displaying the specific information, a method for displaying the specific information in different colors, a method for displaying the specific information using a graphical indicator, a method for displaying the specific information using characters or letters, a method for displaying the specific information using pictures, etc.

As can be seen from FIG. 12, the fact that the first position sensor 210 is separated from the ultrasonic probe 200 is displayed on the display unit 160 using letters or characters, and the user can recognize separation or non-separation of the first position sensor 210 through the screen image of the display unit 160. The display unit 160 includes a touch panel capable of receiving a user input signal through user's touch, such that the user can select the prosecution or termination of inspection by touching the display unit 160.

As can be seen from FIG. 13, specific information indicating that the second position sensor 220 is separated from the ultrasonic probe 200 may be graphically shown along with a warning message, and the user can intuitively recognize whether the second position sensor 220 is separated from the ultrasonic probe 200 through the screen image of the display unit 160. In addition, as can be seen from FIG. 10, the display unit 160 may also display strength of the output signals of the first and second position sensors (210, 220).

Although not shown in the drawings, the ultrasonic imaging apparatus 100 may include the notification unit 170. The control unit 400 controls the notification unit 170, such that the user may be audibly notified of specific information indicating whether at least one of the first and second position sensors (210, 220) is separated from the ultrasonic probe 200.

The notification unit 170 may be mounted to an arbitrary position of the ultrasonic imaging apparatus 100. That is, the notification unit 170 may audibly inform the user of information indicating whether at least one of the first and second position sensors (210, 220) is separated from the ultrasonic probe 200, or may also audibly inform the user of signal strength information of the position sensor. This audible notification may be implemented as a voice signal of the user or may also be implemented as a mechanical sound such as a warning sound.

The notification unit 170 may be a general speaker, or may include a vibration plate capable of outputting only sound as necessary. In addition, there is no limitation in the installation position of the notification unit 170, the notification unit 170 may be installed at an arbitrary position of the ultrasonic imaging apparatus 100, and the main body may also be mounted to one side surface of the input unit 150.

Further, information to be applied to the user through the display unit 160 or the notification unit 170 may also be applied to the user through vibration of the ultrasonic probe 200. That is, when at least one of the first and second position sensors (210, 220) is separated from the ultrasonic probe 200, the user can recognize the separation or non-separation of the position sensor through vibration of the vibration plate mounted to the ultrasonic probe 200.

Figure 14:
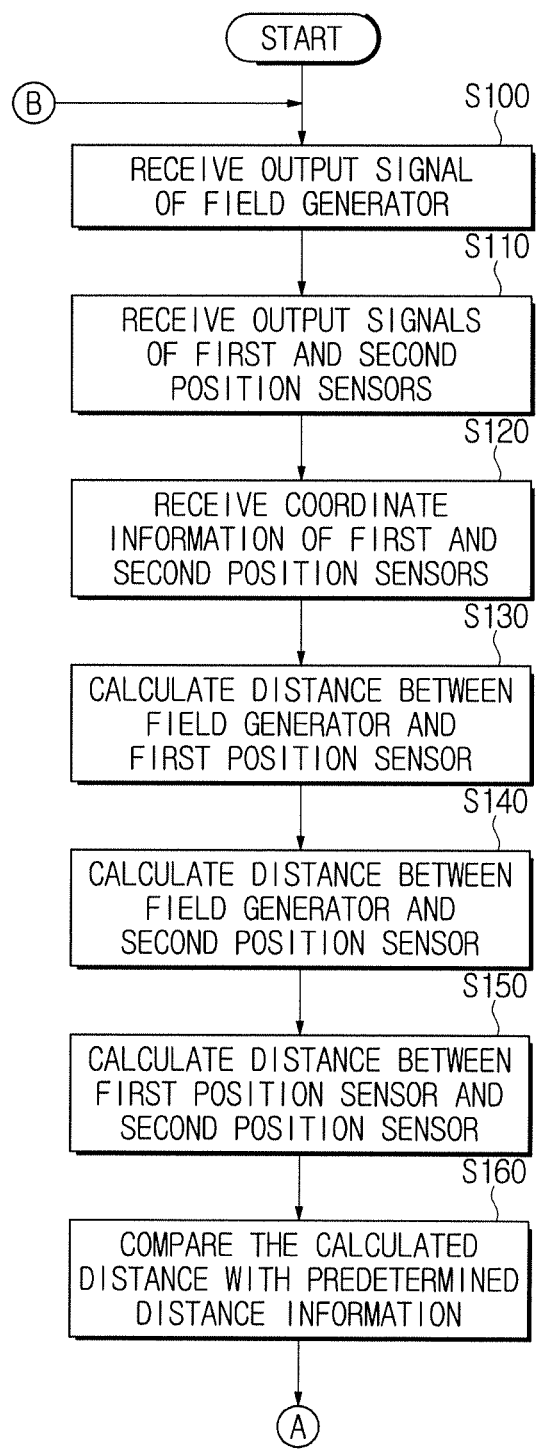
FIGS. 14 to 16 are flowcharts illustrating a method for controlling the ultrasonic imaging apparatus according to an embodiment of the present disclosure.
Figure 15:
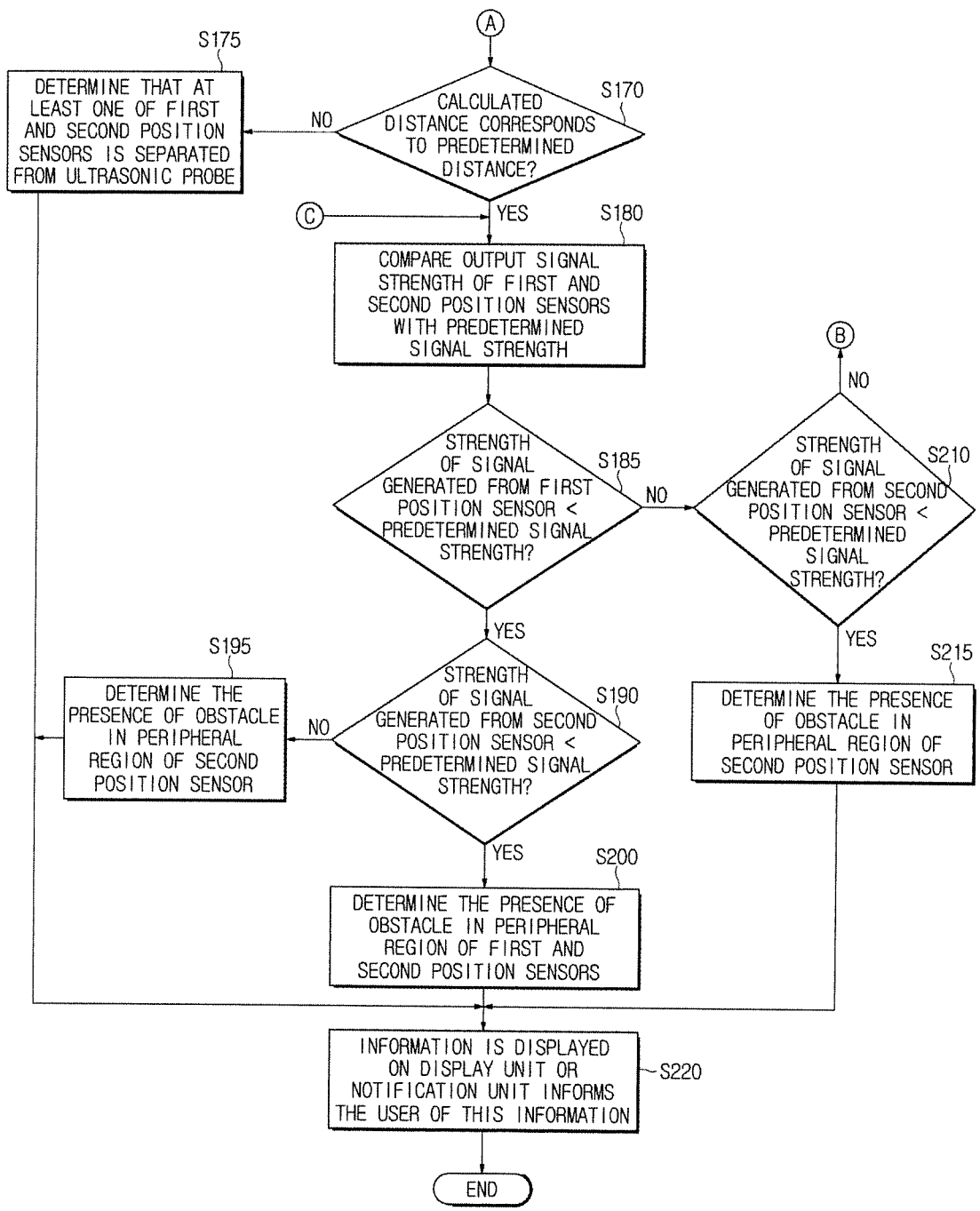
Figure 16:
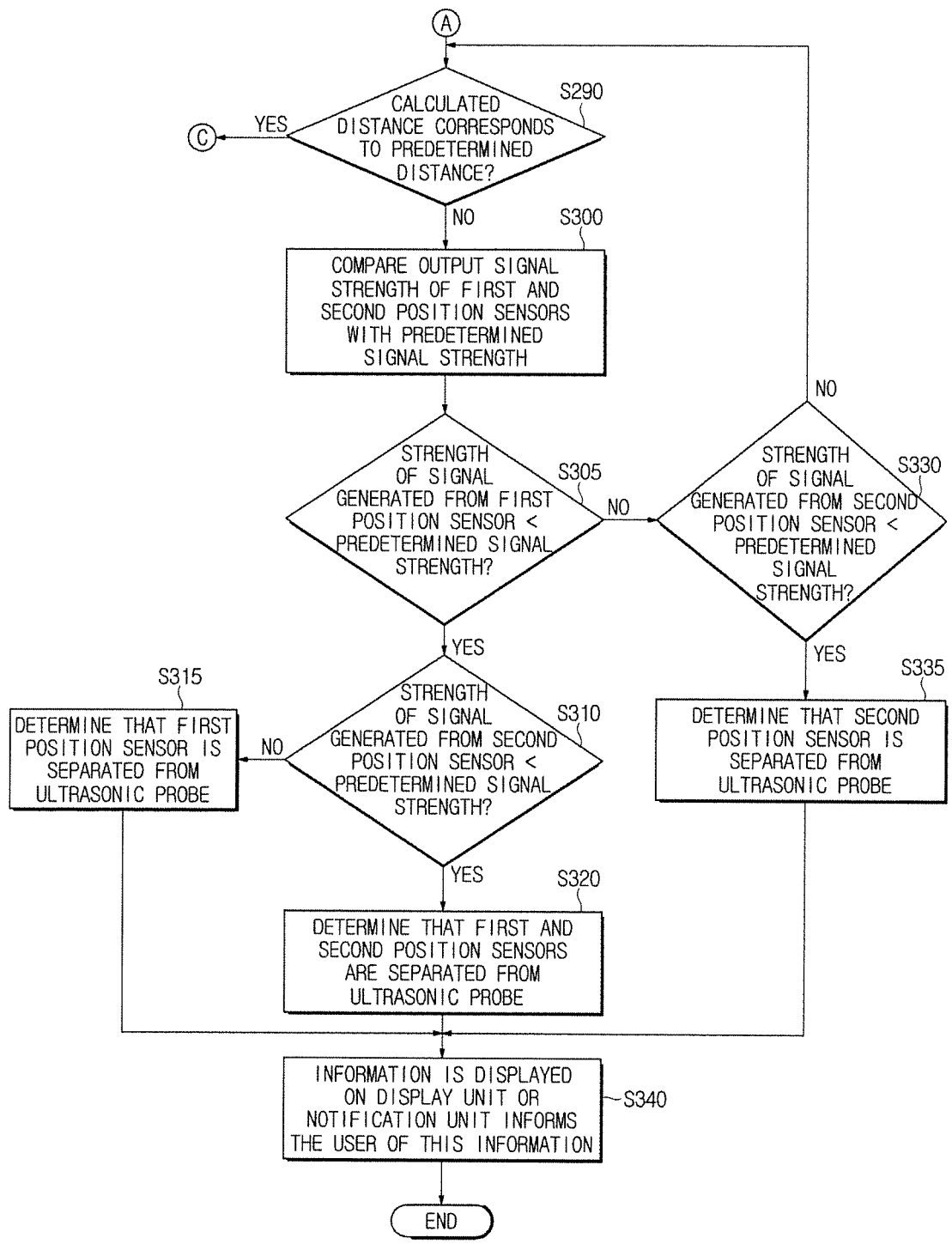

FIGS. 14 to 16 are flowcharts illustrating a method for controlling the ultrasonic imaging apparatus according to an embodiment of the present disclosure.

Referring to FIGS. 14 to 16, the reception unit 147 may receive the output signal of the field generator 800, the output signals of the first and second position sensors (210, 220), and coordinate information of the first and second position sensors (210, 220), and may transmit the received signals to the control unit 400.

The control unit 400 may receive the output signal of the field generator in operation S100, may receive the output signals of the first and second position sensors (210, 220) in operation S110, and may receive coordinate information of the first and second position sensors (210, 220) in operation S120.

The control unit 400 may calculate the distance between the field generator 800 and the first position sensor 210 on the basis of coordinate information of the first position sensor 210 in operation S130, and may calculate the distance between the field generator 800 and the second position sensor 220 on the basis of coordinate information of the second position sensor 220 in operation S140. In addition, the distance between the first position sensor 210 and the second position sensor 220 may be calculated on the basis of coordinate information of the first and second position sensors (210, 220). The calculation method has already been disclosed, and, as such, a detailed description thereof will herein be omitted for convenience of description.

The control unit 400 may calculate the distance between the first position sensor 210 and the second position sensor 220, and may compare the calculated distance with distance information stored in the storage unit 600 in operation S160.

If the calculated distance does not correspond to a predetermined distance according to the comparison result, this means that at least one of the first and second position sensors (210, 220) is separated from the ultrasonic probe 200 in operation S175. If the control unit 400 determines that at least one of the first and second position sensors (210, 220) is separated from the ultrasonic probe 200, the display unit 160 displays specific information indicating the separation or non-separation of the position sensor such that the user can audibly recognize the displayed information.

In this case, the control unit 400 can perform the following control procedure so as to determine which one of the first position sensor 210 and the second position sensor 220 is separated from the ultrasonic probe 200.

First of all, the control unit 400 may compare strength of the output signals of the first and second position sensors (210, 220) with predetermined signal strength in operation S300, and may determine whether the output signal strength of the first position sensor 210 is less than the predetermined signal strength in operation S305 according to the comparison result. If the output signal strength of the first position sensor 210 is less than the predetermined signal strength, the control unit 400 may determine whether the output signal strength of the second position sensor 220 is less than the predetermined signal strength in operation S310.

If the output signal strength of the second position sensor 220 is not less than the predetermined signal strength, the control unit 400 may determine that the second position sensor 220 is not separated from the ultrasonic probe 200 and the first position sensor 210 is separated from the ultrasonic probe 200 in operation S315. In contrast, if the output signal strength of the second position sensor 220 is less than the predetermined signal strength, the control unit 400 may determine that both the first position sensor 210 and the second position sensor 220 are separated from the ultrasonic probe 200 in operation S320.

According to the comparison result in which the output signal strength of the first and second position sensors (210, 220) is compared with the predetermined signal strength, if the output signal strength of the first position sensor 210 is not less than the predetermined signal strength, the control unit 400 may determine whether output signal strength of the second position sensor 220 is less than the predetermined signal strength in operation S330.

If the output signal strength of the second position sensor 220 is not less than the predetermined signal strength, the control unit 400 may re-determine whether the distance between the first position sensor 210 and the second position sensor 220 corresponds to a predetermined distance. If the output signal strength of the second position sensor 220 is less than the predetermined signal strength, the control unit 400 may determine that the second position sensor 220 is separated from the ultrasonic probe 200 in operation S335.

The display unit 160 may determine specific information indicating whether at least one of the first position sensor 210 and the second position sensor 220 is separated from the ultrasonic probe 200, and the notification unit 170 may audibly inform the user of separation or non-separation of the position sensor in operation S340.

The control unit 400 may compare the output signal strength of the first and second position sensors (210, 220) with predetermined signal strength in operation S180, and may determine whether the output signal strength of the first position sensor 210 is less than the predetermined signal strength in operation S185. If the output signal strength of the first position sensor 210 is less than the predetermined signal strength, the control unit 400 may determine whether the output signal strength of the second position sensor 220 is less than the predetermined signal strength in operation S190.

If the output signal strength of the second position sensor 220 is not less than the predetermined signal strength, the control unit 400 may determine that an obstacle configured to affect signal measurement is not present in the peripheral region of the second position sensor 220 and the above obstacle is present in the peripheral region of the first position sensor 210 in operation S195. In contrast, if the output signal strength of the second position sensor 220 is less than the predetermined signal strength, the control unit 400 may determine the presence of the obstacle affecting signal measurement in the peripheral regions of the first and second position sensors (210, 220) in operation S200.

If the output signal strength of the first position sensor 210 is not less than the predetermined signal strength, the control unit 400 may determine whether the output signal strength of the second position sensor 220 is less than the predetermined signal strength in operation S210.

If the output signal strength of the second position sensor 220 is less than the predetermined signal strength, the control unit 400 may determine the presence of the obstacle affecting the signal measurement in the peripheral region of the second position sensor 220 in operation S215.

The display unit 160 may display not only the output signal strength of the first and second position sensors (210, 220), but also specific information indicating whether the obstacle affecting signal measurement is present in the peripheral region of at least one of the first and second position sensors (210, 220). The notification unit 170 may audibly inform the user of the presence or absence of the obstacle in operation S220.

Figure 17:
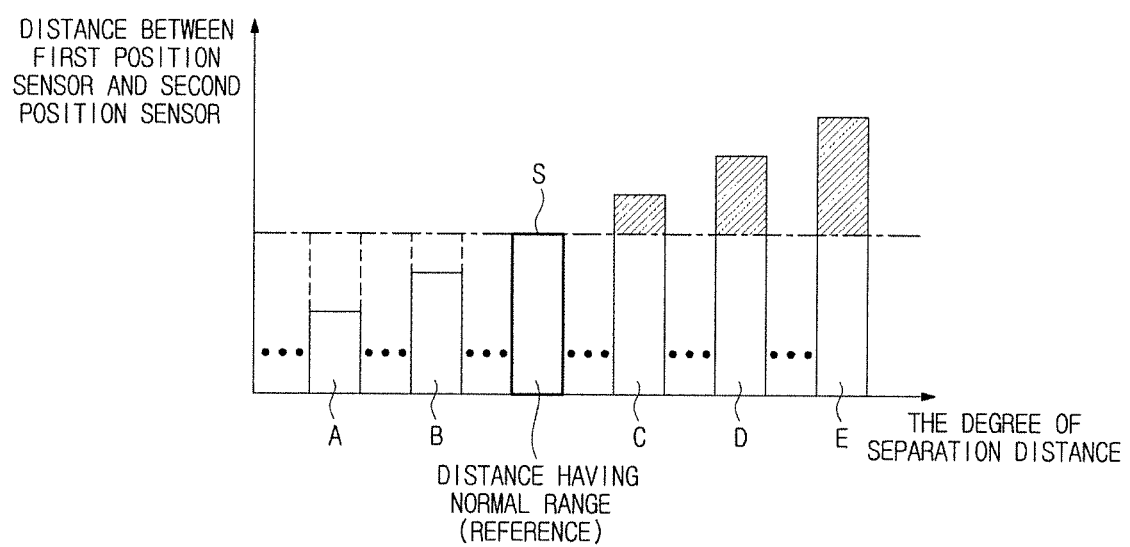
FIG. 17 is a conceptual diagram illustrating a difference in separation distance between the first position sensor and the second position sensor according to an embodiment of the present disclosure.

FIG. 17 is a conceptual diagram illustrating a difference in separation distance between the first position sensor and the second position sensor according to an embodiment of the present disclosure.

Referring to FIG. 17, the control unit 400 may recognize a separation distance between at least one of the first and second position sensors (210, 220) and the ultrasonic probe 200 on the basis of coordinate information of the first and second position sensors (210, 220) mounted to the ultrasonic probe 200, and may compare the separation distance between the separated one of the position sensors and the ultrasonic probe 200 with a reference distance established in the case in which no position sensor is separated from the ultrasonic probe 200 such that the comparison result may be displayed on the screen image.

If the first and second position sensors (210, 220) are not separated from the ultrasonic probe 200, information regarding the reference distance and reference direction between the first position sensor 210 and the second position sensor 220 is stored in the storage unit 600, such that the control unit 400 may calculate the separation distance of at least one of the first and second position sensors (210, 220) on the basis of the reference distance and the reference direction stored in the storage unit 600.

FIG. 17 exemplarily discloses that the separation distance of each of the first position sensor 210 and the second position sensor 220 is displayed on the coordinate plane. In FIG. 17, the separation distances of the first position sensor 210 and the second position sensor 220 are displayed on an X-axis, and a separation distance between the first position sensor 210 and the second position sensor 220 may be displayed on a Y-axis.

Referring to FIG. 17, assuming that the first and second position sensors (210, 220) are not separated from the ultrasonic probe 200, a constant distance may be maintained between the first position sensor 210 and the second position sensor 220. In this case, a reference distance may be denoted by a normal reference distance (S) having a normal range.

If at least one of the first position sensor 210 and the second position sensor 220 is separated from the ultrasonic probe 200, the distance between the first position sensor 210 and the second position sensor 220 may be shorter than the reference distance (S), and the separation degree between the first and second position sensors (210, 220) may be displayed as shown in FIG. 17.

Referring to FIG. 17, the graphs (A, B) may exemplarily display that at least one of the first and second position sensors (210, 220) is separated from the ultrasonic probe 200 such that the separation distance between the first and second position sensors (210, 220) is shorter than the reference distance (S). The graphs (C and D) may exemplarily display that at least one of the first and second position sensors (210, 220) is separated from the ultrasonic probe 200 such that the separation distance between the first and second position sensors (210, 220) is longer than the reference distance (S).

Although FIG. 17 illustrates various exemplary cases in which the first position sensor 210 and the second position sensor 220 are separated from the ultrasonic probe 200 for convenience of description, the separation distance between the first position sensor 210 and the second position sensor 220 when at least one of the first and second position sensors (210, 220) is separated from the ultrasonic probe 200 is shown in FIG. 17.

The A and B graphs exemplarily disclose that the distance between the first position sensor 210 and the second position sensor 220 is shorter than the reference distance (S), and the distance between the first and second position sensors (210, 220) for use in the A graph is shorter than the distance between the first and second position sensors (210, 220) for use in the B graph. In other words, the separation distance between at least one of the first and second position sensors (210, 220) and the ultrasonic probe 200 for use in the A graph is longer than in the B graph.

The C and E graphs may exemplarily disclose that the distance between the first position sensor 210 and the second position sensor 220 is longer than the reference distance (S), and the distance between the first and second position sensors (210, 220) for use in the C graph is longer than in the D graph. In other words, the separation distance between at least one of the first and second position sensors (210, 220) and the ultrasonic probe 200 for use in the C graph is longer than in the D graph. Likewise, the separation distance between the first position sensor 210 and the second position sensor 220 for use in the E graph is longer than in the D graph, and the separation distance between at least one of the first and second position sensors (210, 220) and the ultrasonic probe 200 for use in the E graph is longer than in the D graph.

Accordingly, the user can intuitively recognize the separation distance between the ultrasonic probe 200 and at least one of the first and second position sensors (210, 220) through the screen image as shown in FIG. 17, and can also recognize reliability of diagnosis environment when diagnosing the target object using the ultrasonic probe 200.

Although FIG. 17 exemplarily discloses the separation distance between the first position sensor 210 and the second position sensor 220, assuming that at least one of the first and second position sensors (210, 220) is separated from the ultrasonic probe 200, if the direction of each position sensor based on the position of the field generator 800 is changed or if the mutual distance between the first position sensor 210 and the second position sensor 220 is changed, the changed information may also be graphically shown in FIG. 17.

The above-mentioned embodiments have exemplarily disclosed the ultrasonic imaging apparatus and the method for controlling the same with reference to the attached drawings, the scope or spirit of the present disclosure is not limited thereto, and the above-mentioned embodiments are merely exemplary in all technical aspects.

As is apparent from the above description, the ultrasonic imaging apparatus according to embodiments of the present disclosure determines whether the position sensor mounted to an ultrasonic probe is separated from the ultrasonic probe, and informs a user of separation or non-separation of the position sensor, such that the user can intuitively recognize whether the position sensor is correctly mounted to the ultrasonic probe and ultrasonic diagnosis is currently underway. In addition, the ultrasonic imaging apparatus according to embodiments of the present disclosure can determine the presence or absence of an obstacle in the peripheral region of the position sensor through strength of signals received from the position sensor.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. An ultrasonic imaging apparatus comprising:
a display;
an ultrasonic probe;
a plurality of position sensors detachably coupled to a main body of the ultrasonic probe;
a receiver configured to receive an output signal from a field generator, and to receive coordinate information, corresponding to each of the plurality of position sensors, determined by the plurality of position sensors based on the output signal indicating a location of the field generator; and
a processor configured to determine whether a relative distance between the plurality of position sensors corresponds to a predetermined relative distance based on the coordinate information, to determine that at least one of the plurality of position sensors is separated from the ultrasonic probe when the relative distance does not correspond to the predetermined relative distance, and to control the display to display a notice for separation of the at least one of the plurality of position sensors in response to determining that at least one of the plurality of position sensors is separated from the ultrasonic probe,
wherein the predetermined relative distance is a distance between the plurality of position sensors when coupled to the main body of the ultrasonic probe.

2. The ultrasonic imaging apparatus according to claim 1, wherein the plurality of position sensors include a first position sensor and a second position sensor spaced apart from the first position sensor by the predetermined relative distance.

3. The ultrasonic imaging apparatus according to claim 1, wherein the receiver transmits the output signal received from the field generator and the coordinate information received from the plurality of position sensors to the processor.

4. The ultrasonic imaging apparatus according to claim 2, wherein the processor is configured to calculate a relative distance between the field generator and the first position sensor and a relative distance between the field generator and the second position sensor based on the coordinate information of the first position sensor and the coordinate information of the second position sensor.

5. The ultrasonic imaging apparatus according to claim 2, wherein the processor is configured to calculate the relative distance between the first position sensor and the second position sensor based on the coordinate information of the first position sensor and the coordinate information of the second position sensor.

6. The ultrasonic imaging apparatus according to claim 5, wherein the processor is configured to compare the relative distance between the first position sensor and the second position sensor with the predetermined relative distance.

7. The ultrasonic imaging apparatus according to claim 6, wherein:
if the relative distance between the first position sensor and the second position sensor is shorter or longer than the predetermined relative distance according to the result of comparison, the processor determines that at least one of the first position sensor and the second position sensor is separated from the ultrasonic probe.

8. The ultrasonic imaging apparatus according to claim 3, wherein the processor is configured to determine whether the plurality of position sensors is separated from the ultrasonic probe by comparing strength of signals received from the plurality of position sensors with predetermined signal strength.

9. The ultrasonic imaging apparatus according to claim 8, wherein the processor is configured to determine that at least one of the plurality of position sensors configured to output a signal having strength lower than the predetermined signal strength is separated from the ultrasonic probe.

10. The ultrasonic imaging apparatus according to claim 3, wherein the processor is configured to compare strength of signals received from the plurality of position sensors with predetermined signal strength, and to determine that an obstacle is present in a peripheral region of at least one of the plurality of position sensors configured to output a signal having strength lower than the predetermined signal strength.

11. The ultrasonic imaging apparatus according to claim 1, further comprising:
a speaker, if at least one of the plurality of position sensors is separated from the ultrasonic probe, configured to audibly indicate separation of the at least one of the plurality of position sensors.

12. A method for controlling an ultrasonic imaging apparatus comprising a display, an ultrasonic probe, a receiver, a plurality of position sensors detachably coupled to a main body of the ultrasonic probe, and a processor, the method comprising:
receiving, by the receiver, an output signal from a field generator;
receiving, by the receiver, coordinate information, corresponding to each of the plurality of position sensors, determined by the plurality of position sensors based on the output signal indicating a location of the field generator;
determining, by the processor, whether a relative distance between the plurality of position sensors corresponds to a predetermined relative distance based on the coordinate information
determining, by the processor, that at least one of the plurality of position sensors is separated from the ultrasonic probe when the relative distance does not correspond to the predetermined relative distance; and
controlling the display to display a notice for separation of the at least one of the plurality of position sensors in response to determining that at least one of the plurality of position sensors is separated from the ultrasonic probe,
wherein the predetermined relative distance is a distance between the plurality of position sensors when coupled to the main body of the ultrasonic probe.

13. The method according to claim 12, wherein the receiving the coordinate information of the plurality of position sensors includes:
receiving coordinate information of a first position sensor; and
receiving coordinate information of a second position sensor spaced apart from the first position sensor by the predetermined relative distance.

14. The method according to claim 13, further comprising:
calculating a relative distance between the field generator and the first position sensor and a relative distance between the field generator and the second position sensor based on the coordinate information of the first position sensor and the coordinate information of the second position sensor,
calculating the relative distance between the first position sensor and the second position sensor based on the coordinate information of the first position sensor and coordinate information of the second position sensor.

* * * * *